US010421072B2

(12) United States Patent
Megaridis et al.

(10) Patent No.: US 10,421,072 B2
(45) Date of Patent: Sep. 24, 2019

(54) WETTABILITY PATTERNED SUBSTRATES FOR PUMPLESS LIQUID TRANSPORT AND DRAINAGE

(71) Applicant: THE BOARD OF TRUSTEES OF THE UNIVERSITY OF ILLINOIS, Urbana, IL (US)

(72) Inventors: Constantine M. Megaridis, Oak Park, IL (US); Ranjan Ganguly, Oak Park, IL (US); Aritra Ghosh, Chicago, IL (US); Thomas Schutzius, Tinley Park, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 374 days.

(21) Appl. No.: 15/112,958

(22) PCT Filed: Jan. 21, 2015

(86) PCT No.: PCT/US2015/012302
§ 371 (c)(1),
(2) Date: Jul. 20, 2016

(87) PCT Pub. No.: WO2015/112635
PCT Pub. Date: Jul. 30, 2015

(65) Prior Publication Data
US 2016/0339424 A1  Nov. 24, 2016

Related U.S. Application Data

(60) Provisional application No. 62/039,747, filed on Aug. 20, 2014, provisional application No. 61/938,481, (Continued)

(51) Int. Cl.
*B01L 3/00* (2006.01)
*G01N 1/10* (2006.01)
*G01N 15/10* (2006.01)

(52) U.S. Cl.
CPC ..... *B01L 3/50273* (2013.01); *B01L 3/502707* (2013.01); *B01L 3/502746* (2013.01);
(Continued)

(58) Field of Classification Search
CPC ......... B01L 2200/0605; B01L 2200/12; B01L 2300/0816; B01L 2300/0864;
(Continued)

(56) References Cited

U.S. PATENT DOCUMENTS 6,033,546 A  3/2000 Ramsey
6,042,710 A  3/2000 Dubrow
(Continued)

OTHER PUBLICATIONS

Ghosh et al. Lab Chip, vol. 14, Mar. 13, 2014, pp. 1538-1550.*
(Continued)

*Primary Examiner* — Maureen Wallenhorst
(74) *Attorney, Agent, or Firm* — Michael Best & Friedrich LLP

(57) ABSTRACT

Provided herein are methods and materials for the manufacture and use of wettability tracks on various substrates for rapid fluid transport and drainage, even in a condensing environment. The degree of wettability of the materials' surfaces range from superhydrophobic to superhydrophilic. The method centers on the formation of a dispersion of titanium dioxide and a fluoroacrylic co-polymer in an alcohol and water solution. The dispersion may then be deposited onto a surface to form a coating, which is then dried to evaporate the alcohol. The dried coating is exposed to radiation to produce a wedge-shaped track. The coating is exposed to the radiation through a photomask to produce the
(Continued)

(a)  (b)

track. The radiation may be high energy, such as UV radiation. The radiation may be selectively exposed to designated areas on the coating. The hydrophilic wedge-shaped track may have a wedge angle of from 0 degrees to 45 degrees.

10 Claims, 24 Drawing Sheets

Related U.S. Application Data filed on Feb. 11, 2014, provisional application No. 61/929,860, filed on Jan. 21, 2014.

(52) U.S. Cl.
CPC ... *B01L 2200/0605* (2013.01); *B01L 2200/12* (2013.01); *B01L 2300/089* (2013.01); *B01L 2300/0816* (2013.01); *B01L 2300/0864* (2013.01); *B01L 2300/0883* (2013.01); *B01L 2300/12* (2013.01); *B01L 2300/126* (2013.01); *B01L 2300/161* (2013.01); *B01L 2300/166* (2013.01); *B01L 2400/0406* (2013.01); *B01L 2400/088* (2013.01); *G01N 2015/1006* (2013.01); *Y10T 436/2575* (2015.01)

(58) Field of Classification Search
CPC ....... B01L 2300/0883; B01L 2300/089; B01L 2300/12; B01L 2300/126; B01L 2300/161; B01L 2300/166; B01L 2400/0406; B01L 2400/088; B01L 3/502707; B01L 3/50273; B01L 3/502746; G01N 2015/1006; Y10T 436/2575
USPC .......................... 422/502, 503, 507; 436/180
See application file for complete search history.

(56) References Cited

U.S. PATENT DOCUMENTS

| | | | |
|---|---|---|---|
| 6,045,676 | A | 4/2000 | Mathies et al. |
| 6,046,056 | A | 4/2000 | Parce et al. |
| 6,383,559 | B1 | 5/2002 | Nakamura et al. |
| 6,517,234 | B1 | 2/2003 | Kopf-Sill et al. |
| 8,921,118 | B2 * | 12/2014 | Siegel ............... B01L 3/502707 422/412 |
| 9,139,739 | B2 | 9/2015 | Megaridis et al. |
| 2007/0231559 | A1 | 10/2007 | Kim et al. |
| 2008/0221263 | A1 | 9/2008 | Kanagasabapathy et al. |
| 2009/0018249 | A1 | 1/2009 | Kanagasabapathy et al. |
| 2009/0064894 | A1 | 3/2009 | Baumgart et al. |
| 2010/0143741 | A1 | 6/2010 | Bell et al. |
| 2010/0316842 | A1 * | 12/2010 | Tuteja ............... D01D 5/003 428/143 |
| 2011/0177252 | A1 | 7/2011 | Kanagasabapathy et al. |
| 2011/0319300 | A1 | 12/2011 | Hunter et al. |
| 2012/0009429 | A1 | 1/2012 | Shmueli et al. |
| 2012/0276544 | A1 | 11/2012 | Quake et al. |
| 2013/0178568 | A1 | 7/2013 | Meuler et al. |
| 2014/0017457 | A1 * | 1/2014 | Megaridis ................ C09D 1/00 428/195.1 |
| 2015/0132742 | A1 * | 5/2015 | Thuo ................ B01L 3/502707 435/5 |

OTHER PUBLICATIONS

Bell et al., "Coating a metallic article, e.g. heat transfer sheets of heat exchanger, by coating metal layer with silver or gold to provide a metal-metal bonded surface, and contacting alkylamines, arylamines, phosphines, pyrroles, or thiophenes," The Queen'S University of Belfast, Belfast, United Kingdom, published Jun. 10, 2010.
Chiou et al., "Growth and alignment of polyaniline nanofibres with superhydrophobic, superhydrophilic and other properties," Nature Nanotechnology 2, 354-357 (2007).
Kanagasabapathy et al., "Coating on surface e.g. metal, where coating has specific contact angle is formed by applying nanoparticles of silsesquioxane having adhesion promoter and low surface energy groups dispersed in solvent to surface, and evaporating solvent," Ashland Licensing and Intellectual Property LLC, Dublin, OH, published Jul. 21, 2011.
Lai, et al., "Superhydrophilic-superhydrophobic micropattern on TiO2 nanotube films by photocatalytic lithography," Electrochemistry Communications, vol. 10, Issue 3, Mar. 2008, pp. 387-391.
Rafiee, et al., "Superhydrophobic to Superhydrophilic Wetting Control in Graphene Films," Advanced Materials vol. 22, Issue 19, pp. 2151-2154, May 18, 2010.
Tadanaga et al., "Superhydrophobic-Superhydrophilic Micropatterning on Flowerlike Alumina Coating Film by the Sol-Gel Method," Chem. Mater. 2000, 12, 590-592.
Schutzius et al., "Superhydrophobic-superhydrophilic binary micropatterns by localized thermal treatment of polyhedral oligomeric silsesquioxane (POSS)-silica films," Nanoscale, 4, pp. 5378-5395, 2012.
Shirtcliffe et al., "Porous materials show superhydrophobic to superhydrophilic switching," Chem. Commun, pp. 3135-3137, 2005.
Chen et al., "Perfectly Hydrophobic Silicone Nanofiber Coatings: Preparation from Methyltrialkoxysilanes and Use as Water-Collecting Substrate," J Phys. Chem., 113, pp. 8350-8356, 2009.
Weng et al., "Advanced anticorrosion coating materials prepared from fluoro-polyaniline-silica composites with synergistic effect of superhydrophobicity and redox catalytic capability," Surface and Coatings Technology, 207, pp. 42-49, 2012.
United States Patent Office Action for U.S. Appl. No. 13/942,494 dated Jul. 23, 2014 (10 pages).
United States Patent Office Final Rejection for U.S. Appl. No. 13/942,494 dated Mar. 6, 2015 (10 pages).
United States Patent Office Notice of Allowance for U.S. Appl. No. 13/942,494 dated Jun. 17, 2015 (7 pages).
International Search Report and Written Opinion for U.S. Appl. No. PCT/US2015/12302 dated Jun. 25, 2015 (21 pages).
Aarts, et al., "Hydrodynamics of Droplet Coalescence," Phys. Rev. Lett., 2005, 95, 164503.
Alheshibri et al., "Spontaneous movement of water droplets on patterned Cu and Al surfaces with wedge-shaped gradients," Appl. Physics Lett., 2013, 102, 174103.
Balu, et al., "Patterning of superhydrophobic paper to control the mobility of micro-liter drops for two-dimensional lab-on-paper applications," Lab Chip, 2009, 9, 3066-3075.
Bliznyuk, et al., "Smart Design of Stripe-Patterned Gradient Surfaces to Control Droplet Motion," Langmuir, 2011, 27, 11238-11245.
Brinkmann and R. Lipowsky, "Wetting morphologies on substrates with striped surface domains," J. Appl. Phys., 2002, 92, 4296-4306.
Cassie, S. Baxter, "Wettability of Porous Surfaces," Trans. Faraday Society 1944, 40, 546-551.
Chandesris et al., "Uphill motion of droplets on tilted and vertical grooved substrates induced by a wettability gradient," Colloids Surfaces A: Physicochem. Eng. Aspect, 2013, 434, 126-135.
Chen, Y. Nagamine and K. Yoshikawa, "Self-propelled motion of a droplet induced by Marangoni-driven spreading," Physical Rev. E, 2009, 80, 016303.
Cheng and Chen, "Adaptive Chip Cooling Using Electrowetting on Coplanar Control Electrodes," Nanoscale Microscale Thermophysical Eng., 2010, 14, 63-74.
Chitnis et al., "Laser-treated hydrophobic paper: an inexpensive microfluidic platform," Lab Chip, 2011, 11, 1161-1165.
Choi et al., "Digital Microfluidics," Ann. Rev. Anal. Chem., 2012, 5, 413-440.
Choudhury and Whitesides, "How to Make Water Run Uphill," Science, 1992, 256, 1539-1541.

(56) References Cited

OTHER PUBLICATIONS

Darhuber and S. M. Troian, "Principles of Microfluidic Actuation by Modulation of Surface Stresses," Ann. Rev. Fluid Mech., 2005, 37, 425-455.
Darhuber, "Thermocapillary Actuation of Droplets on Chemically Patterned Surfaces by Programmable Microheater Arrays," Microelectromech. Syst., 2003, 12, 873-879.
Eiswirth et al., "Experimental and numerical investigation of binary coalescence: Liquid bridge building and internal flow fields," Physics Fluids, 2012, 24, 062108.
Foresti et al., "Acoustophoretic contactless transport and handling of matter in air," Proc. Nat. Academey Sci., 2013, 110, 12494-12554.
Gau et al., "Liquid Morphologies on Structured Surfaces: From Microchannels to Microchips," Science, 1999, 283, 46-49.
Göröcs et al., "Giga-pixel fluorescent imaging over an ultra-large field-of-view using a flatbed scanner," Lab Chip, 2013, 13, 4460-4466.
Hirayanagi et al., "Micro Thermal Diode with Glass Thermal Insulation Structure Embedded in Vapor Chamber," Journal of Physics: Conference Series, 2013, 476, 012019.
Jokinen et al., "Complex Droplets on Chemically Modified Silicon Nanograss," Adv. Mater., 2008, 20, 3453-3456.
Jokinen et al., "Multiphase Designer Droplets for Liquid-Liquid Extraction," Adv. Mater., 2012, 24, 6240-6243.
Kandlikar, "Microscale and Macroscale Aspects of Water Management Challenges in PEM Fuel Cells," Heat Transfer Eng., 2008, 29, 575-587.
Khoo and F.-G. Tseng, "Spontaneous high-speed transport of subnanoliter water droplet on gradient nanotextured surfaces," Appl. Phys. Lett., 2009, 95, 063108.
Kim et al., "Drop impact on super-wettability-contrast annular patterns," J. Fluid Mech., 2013, 730, 328-342.
Kooij et al., "Directional wetting on chemically patterned substrates," Colloids Surfaces A: Physicochem. Eng. Aspect, 2012, 413, 328-333.
Kusumaatmaja and R. Lipowsky, "Equilibrium Morphologies and Effective Spring Constants of Capillary Bridges,"Langmuir, 2010, 26, 18734-18741.
Lai et al., "A microchip fabricated with a vapor-diffusion self-assembled-monolayer method to transport droplets across superhydrophobic to hydrophilic surfaces," Lab Chip, 2010, 10, 499-504.
Lee et al., "Drop impact on microwetting patterned surfaces," Phys. Fluids, 2010, 22, 072101.

Long, "Fundamentals of magnet-actuated droplet manipulation on an open hydrophobic surface," Lab Chip, 2009, 9, 1567-1575.
Lorenceau and D. Quéré, "Drops on a conical wire," J. Fluid Mech., 2004, 510, 29-45.
Lv and P. Hao, "Driving Droplet by Scale Effect on Microstructured Hydrophobic Surfaces," Langmuir, 2012, 28, 16958-16965.
Martinez et al., "Patterned Paper as a Platform for Inexpensive, Low-Volume, Portable Bioassays," Angew. Chem., Int. Ed., 2007, 46, 1318-1320.
Mertaniemi et al., "Superhydrophobic Tracks for Low-Friction, Guided Transport of Water Droplets," O. Ikkala and R.H.A. Ras, Adv. Mater., 2011, 23, 2911-2914.
Nakajima et al., "Sliding of Water Droplets on Smooth Hydrophobic Silane Coatings with Regular Triangle Hydrophilic Regions," T. Isobe and S. Matsuhita, Langmuir, 2013, 29, 9269-9275.
Nelson and C.-J. Kim, "Droplet Actuation by Electrowetting-on-Dielectric (EWOD): A Review," J. Adhesion Sci. Tech., 2012, 26, 1747-1771.
Park, "Single-sided continuous optoelectrowetting (SCOEW) for droplet manipulation with light patterns," Lab Chip, 2010, 10, 1655-1661.
Quéré, "Wetting and Roughness," Annu. Rev. Mater. Res., 2008, 38, 71-99.
Santos and T. Ondarçuhu, "Free-Running Droplets," Phys. Rev. Lett., 1995, 75, 2972-2974.
Schutzius et al.,"Surface tension confined (STC) tracks for capillary-driven transport of low surface tension liquids," Lab Chip, 2012, 12, 5237-5242.
Sommers et al., "Topography-Based Surface Tension Gradients to Facilitate Water Droplet Movement on Laser-Etched Copper Substrates," Langmuir, 2013, 29, 12043-12050.
Takeuchi et al., "Mechanism of Photoinduced Superhydrophilicity on the TiO2 Photocatalyst Surface," J. Phys. Chem. B, 2005, 109, 15422.
Wang and J. Zhe, "Recent advances in particle and droplet manipulation for lab-on-a-chip devices based on surface acoustic waves," Lab Chip, 2011, 11, 1280-1285.
Xing et al., "Interfacial microfluidic transport on micropatterned superhydrophobic textile," Lab Chip, 2013, 13, 1937-1947.
Xing et al., "Droplet-driven transports on superhydrophobic-patterned surface microfluidics," Lab Chip, 2011, 20, 3642-3648.
Yang, "Facile control of surface wettability in TiO2/poly(methyl methacrylate) composite films," J. Colloids Interface Sci., 2013, 368, 603-607.
Yang et al., "Conversion of Surface Energy and Manipulation of a Single Droplet across Micropatterned Surfaces," Langmuir, 2008, 24, 9889-9897.

\* cited by examiner

| Contact angles for the different regions of the Type I and Type II substrates | | | |
|---|---|---|---|
| | CONTACT ANGLE | ADVANCING ANGLE | RECEDING ANGLE |
| Bare Aluminum | 78.2° ± 2° | 106.8° ± 1° | 72.8° ± 4° |
| FAS-Coated Al | 163.8° ± 1° | 167.4° ± 3° | 153.7° ± 2° |
| Superhydrophilic Al (chemically treated, water boiled) | *  | * | * |

* CA values too low to measure

WETTABILITY PATTERNED SUBSTRATES FOR PUMPLESS LIQUID TRANSPORT AND DRAINAGE

CROSS-REFERENCE TO RELATED APPLICATIONS

This is a U.S. national stage entry of International Patent Application No. PCT/US2015/012302, filed on Jan. 21, 2015, which claims priority to U.S. Provisional Patent Application No. 62/039,747, filed on Aug. 20, 2014, U.S. Provisional Patent Application No. 61/938,481, filed on Feb. 11, 2014, and U.S. Provisional Patent Application No. 61/929,860, filed on Jan. 21, 2014, the entire contents of all of which are fully incorporated herein by reference.

STATEMENT OF GOVERNMENT INTEREST

This invention was made with government support under Grant No. 1331817 awarded by the National Science Foundation through its Small Business Technology Transfer (STTR) Program. The government has certain rights in the invention.

FIELD OF THE INVENTION

The present invention relates to the manufacture and use of wettability tracks and patterns on various substrates. The degree of wettability of the coating ranges from very low (superhydrophobic) to very high (superhydrophilic).

BACKGROUND

The wettability of a material is dependent on both its physical and chemical characteristics. If a liquid spreads completely across the surface of a material and forms a film, the contact angle, $\theta$, is close to 0 degrees (°). Such a surface may be said to be superhydrophilic. If the liquid beads on the surface, the surface is considered to be non-wettable by this specific liquid. For water, the substrate surface is considered to be hydrophobic if the contact angle is greater than 90°. Certain applications may require a hydrophobic coating with a high contact angle of at least 150°. These coatings may be said to be superhydrophobic.

Microfluidic systems on planar chips have gained popularity for handling miniscule volumes of liquids on the surface of open substrates. Open microfluidics offers a promising mode of digital microfluidics, which involves manipulating individual droplets without the need for dedicated components like microchannels, pumps, valves, sorters or mixers. Handling liquid on open substrates also minimizes the contact between the fluid and the channel walls, thus eliminating the risk of air-bubble clogging, fouling by debris and nonspecific surface adsorption of reagents. Besides, handling isolated droplets on the digital microfluidic platform minimizes cross-contamination between samples. However, achieving regular microfluidic tasks (e.g., sample drawing, metering, merging and dispensing) in a controlled fashion remains a challenge when using open microfluidic systems. Discrete microfluidic liquid transport technology has been achieved by electrowetting-on-dielectric (EWOD), optoelectrowetting (OEW), magnetic force, gravity, thermocapillarity, or acoustic vibrations. Surface wettability has played a supportive role in most of these applications by ensuring the desired droplet mobility and controllability. However, these active technologies require continuous power supply (or a desired orientation of the substrates in case of gravity-driven transport), and elaborate on-chip/off-the-chip interfacing arrangements (e.g., electrode array, permanent magnet assembly, sub-surface heating, etc.)—which for some applications are necessary—but they make their implementation more difficult.

Pumpless liquid transport technologies play an important role in the process of condensation. For example, condensation is not only ubiquitous in nature (rain from clouds), but it also plays a great role in large spectrum of engineering applications, starting from heat exchangers in power and process industries to fuel cells, from electronic thermal management to HVAC as well as water harvesting from the open atmosphere. From a thermodynamic perspective, achieving high condensation heat flux under minimum driving temperature difference (between the gas environment and the surface) is most desirable, because this improves the efficiency of energy conversion devices. Condensation heat transfer occurs in two primary modes, dropwise condensation (DWC) and filmwise condensation (FWC), the former offering an order of magnitude higher heat transfer coefficient (HTC) than the latter. HTC is a metric that, when maximized, allows optimal heat transfer operation, and thus maximum energy savings. However, achieving sustained DWC in engineering applications has remained an elusive task despite intense research for over half a century.

The overall performance of DWC depends on several factors, such as droplet nucleation density and rate, maximum size of departing droplets and rapid condensate drainage. It is desirable to design wettability patterned surface capable of controlling all the above three key factors (i.e., achieving optimal spatial nucleation, minimizing the departing droplet size and facilitating rapid drainage of condensate) necessary for enhancement of DWC. Still further, for low-cost microfluidics applications, a substrate-independent, yet straightforward surface preparation approach is desirable.

SUMMARY OF THE INVENTION

Provided herein is a method for preparing wettability tracks on a substrate. The method may center on the formation of a dispersion of titanium dioxide and a fluoroacrylic co-polymer in an alcohol and water solution. The dispersion may then be deposited onto a surface to form a coating, which is then dried to evaporate the alcohol. The dried coating may be exposed to radiation to produce a wedge-shaped track. The coating may be exposed to the radiation through a photomask to produce the track. The radiation may be high energy, such as UV radiation. The radiation may be selectively exposed to designated areas on the coating. The hydrophilic wedge-shaped track may have a wedge angle of from 0° to 45°. The wedge angle may be 3° or 4°. The alcohol may be a mixture of one or more of methanol, n-butanol, ethanol, and isopropanol. The surface may be steel, aluminum, paper, copper, quartz, glass, plastic, fabric, or silicon. The steel may be stainless steel.

The dispersion may contain at least 75% by weight of the titanium dioxide. The dispersion may be deposited onto a surface via spray deposition. The coating may exhibit an advancing contact angle of at least 150°. The advancing contact angle of the hydrophilic area may be less than 5°. The advancing contact angle of the hydrophilic area may be less than 3°. The hydrophilic wedge track may be a superhydrophilic wedge track. The dispersion may be formed via sonication. The sonication may be performed under ambient conditions for between 30 seconds and 5 minutes.

Also provided herein is a composition formed by the method for preparing a wettability track on a substrate.

Also provided herein is a method for pumpless fluid transport on a substrate. The method may comprise applying a drop of liquid fluid to the narrow end of the wedge-shaped track of the composition prepared by the methods described herein, whereby the drop is transported toward the wider end of the wedge-shaped track. The track may be presuffused (pre-wetted) prior to applying the drop of liquid that is intended to be transported. The track may be a level (horizontal) track. The track may be inclined. The angle of the incline may be from 0.5° to 45°. The drop of liquid may be from 2.0 µL to 100 µL. The drop of liquid may be applied to the track via a metered dispensing mechanism. Two or more tracks may merge, thereby merging two or more droplets of liquid. The track may split into two or more tracks, thereby splitting one or more droplets of liquid.

In another embodiment, the method may comprise applying a drop of liquid to a hydrophilic track on a hydrophobic surface, whereby the drop is transported away from the point of application. The hydrophilic track may be confined by the hydrophobic surface. The track may be a wedge-shaped track and the drop of liquid is transported toward the wider end of the wedge-shaped track. The track may be presuffused (pre-wetted) prior to the application of the drop of liquid. The track may be level (horizontal track) or inclined. The angle of the incline may be from 0.5° to 45°. The drop of liquid may be from 2.0 µl to 100 µl. The drop of liquid may be applied to the track via a metered dispensing mechanism. The track may direct the merging of two or more droplets of liquid. The track may split, resulting in the splitting of one or more droplets of liquid. The track may be formed from one or more geometrical hydrophilic shapes produced by the radiation. The shapes may be selected from the group consisting of dots, spheres, wedges, ellipses, squares, rectangles, trapezoids, and combinations thereof. The track or tracks on the substrate may form a pattern. More than one hydrophilic track may be produced on the surface. The resultant wettability track or tracks on the substrate form a pattern. The pattern may be curved (e.g. a spiral). The pattern may direct the merging of two or more droplets of liquid. The pattern may direct the splitting of one or more droplets of liquid.

Also provided herein is a composition comprising a dispersion of titanium dioxide and a fluoroacrylic co-polymer in an alcohol. The dispersion may comprise between 1 wt % and 25 wt % of fluoroacrylic co-polymer, between 0.01 wt % and 10 wt % of titanium dioxide, and between 50 wt % and 99.5 wt % of ethanol.

Also provided herein is a composition comprising a substrate that has at least one surface of two alternating domains of contrast wettability. At least one of the domains is superhydrophilic. The two alternating domains may be interdigitated. The two alternating domains may be arranged in parallel strips or tracks (striped patterning). The domains may be superhydrophilic and superhydrophobic (referred to as Type I surface in the rest of this document) or superhydrophilic and hydrophilic (designated as Type II surface), for example. The substrate may be a metal. For example, the metal may be aluminum, which may be a mirror-finish aluminum. The superhydrophilic track(s) may be wedge-shaped. A collection of alternately patterned domains may be laid on periodically on the substrate. The hydrophilic domain may be a strip that is from 300 µm to 3000 µm wide. The superhydrophilic domain may be a strip that is from 200 µm to 500 µm wide.

Also provided herein is a method for pumpless fluid transport on a substrate in condensing ambient conditions (i.e. containing vapor of a condensable substance, such as water). The method comprises exposing a composition comprising a substrate having a surface of two alternating domains of contrast wettability (biphilic) to a condensing environment, wherein one of the domains is superhydrophilic. The vapor may then condense and nucleate and grow as a drop of liquid on the less wettable domain of the surface (the surface that is not superhydrophilic). The growing drop will grow, and transition across the wettability contrast line that separates the less wettable domain of the surface and the superhydrophilic domain. Once the drop has crossed into the superhydrophilic domain, the drop is transported away by the film from the point of transition. The condensing environment may have a relative humidity of above 10%. The condensing environment may have a temperature of from 5° C. to 200° C. The two alternating domains may be interdigitated. The two alternating domains may be arranged in parallel strips or tracks (striped biphilic patterning). The wettability contrast domains may be superhydrophilic and superhydrophobic or superhydrophilic and hydrophilic, for example. The substrate may be a metal. For example, the metal may be aluminum, which may be a mirror-finish aluminum. The superhydrophilic track(s) may be wedge-shaped. The hydrophilic domain may be a strip that is from 300 µm to 3000 µm wide. The superhydrophilic domain may be a strip that is from 200 µm to 500 µm wide. The method for pumpless fluid transport on a substrate in condensing conditions may also control maximum droplet size of the condensate. The maximum size of the drop may be linearly related to the width of the superhydrophilic domain or track.

BRIEF DESCRIPTION OF THE DRAWINGS

[FIG. 25(*b*) reprinted with permission from J. Brittin, www.jamesbrittin.com]

DETAILED DESCRIPTION

Figure 1:
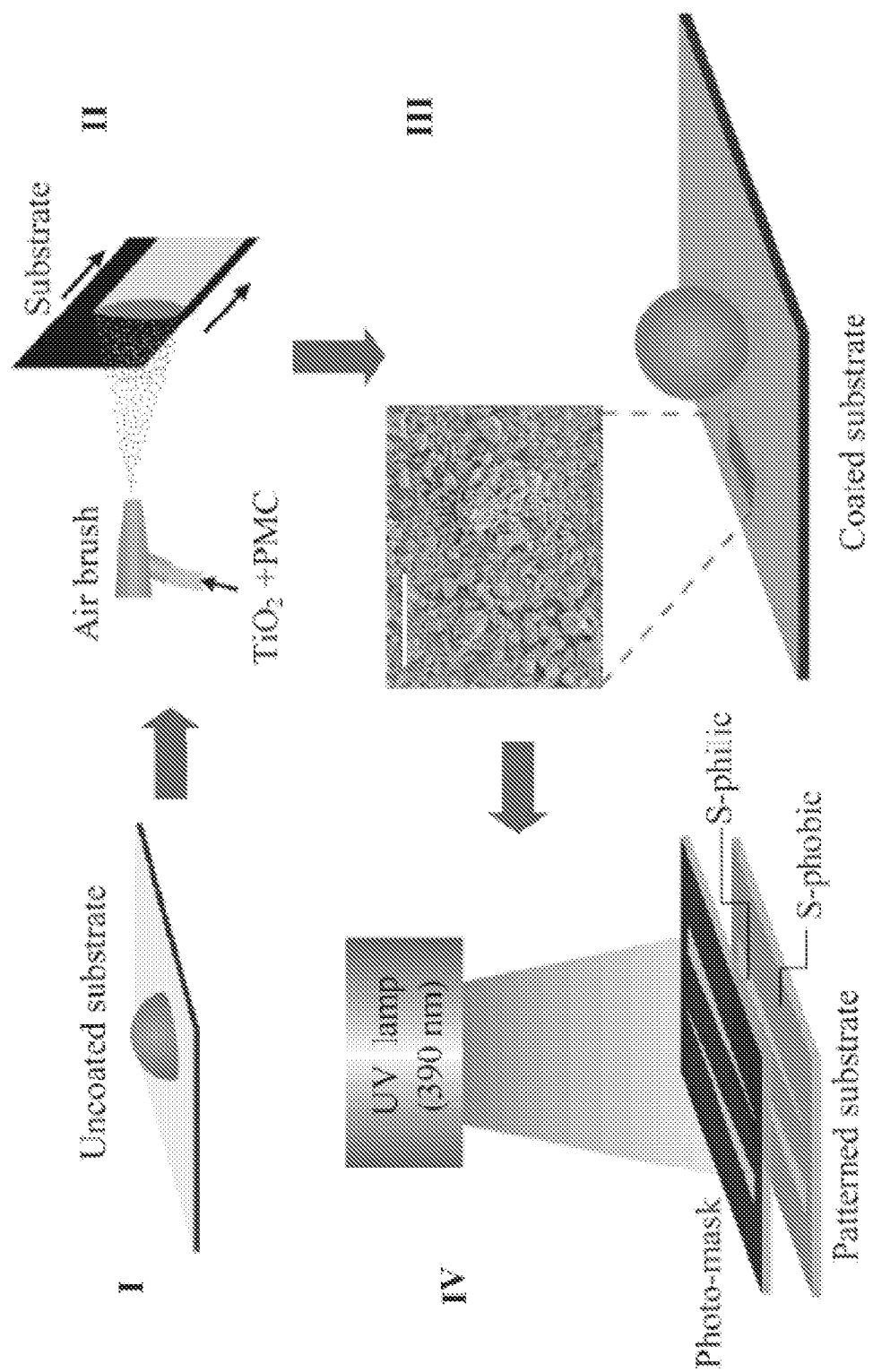
FIG. 1 shows salient steps of surface preparation. (I) Uncoated substrate (e.g. aluminum, polyethylene terephthalate, PET film or regular white paper). (II) Spray-coating of $TiO_2$-PMC aqueous suspension on substrate. (III) Coated substrate, and SEM image of the coated surface showing the different length scales of the deposited nanoparticle composite coating. Combination of PMC and the roughness imparted by the $TiO_2$ particles renders the surface superhydrophobic (water beads). (IV) UV treatment of the superhydrophobic substrate through a patterned photomask to form the superhydrophilic regions. Exposed regions turn superhydrophilic (S-philic) upon 30 minutes of exposure to UV, while the unexposed regions remain superhydrophobic (S-phobic).

The inventors have developed a facile, substrate independent, wettability patterning method for the controlled pumpless transport of liquid. The liquid may be transported on flat or inclined substrates without adding external energy. For example, the fluid may be transported via self-driven processes. At the center of the method is a surface having at least some portions of two alternating domains of contrast wettability (biphilic). At least one of the domains may be hydrophilic or superhydrophilic. The geometry or shape and size of the domains, and their arrangement in relation to one another, may influence that rate of liquid transport.

The hydrophilic domain may be a planar track or a wedge-shaped planar track, which may be laid on a hydrophobic background. Liquid dispensed or condensing at the narrow ends of a hydrophilic wedge track is transported to the wider ends. The transport may be driven by hemiwicking, gravity, and/or Laplace pressure. The driving capillary force may increase linearly with the wedge-angle of the tracks. The hydrophilic planar track may be superhydrophilic. The hydrophobic background may be superhydrophobic.

The wettability patterning method is useful for preparing a wettability track on a substrate. A dispersion of titanium oxide and a fluoroacrylic co-polymer in an alcohol solvent is deposited onto a surface to form a coating, which is then dried. The coating may then be subjected to localized radiation, for example through photomask, which may produce a hydrophilic wedge-shaped or tapered track. The radiation may be UV radiation, for example. The resultant track is capable of inducing controlled on-chip movement of aqueous liquid volumes with characteristic size comparable to the capillary length $\kappa^{-1}=\sqrt{\gamma/\rho g}$ (γ denoting the liquid surface tension, ρ its density and g the acceleration due to gravity), by overcoming viscous and other opposing forces (e.g., gravity). The concept is developed and demonstrated with coatings based on $TiO_2$ powder, which, when present in optimum quantities within a hydrophobic polymer matrix, forms composites that are intrinsically superhydrophobic. Such composite coatings become superhydrophilic upon exposure to UV light. Thus, a masking process can facilitate spatially-selective conversion from superhydrophobic to superhydrophilic behavior, which is used herein to fabricate open-air devices that can move fluid efficiently without external power input. Simple design features of wettability patterning have been used on versatile substrates (e.g., metals, polymers or paper) to demonstrate complex droplet handling tasks, some of which are in 3-D geometries. The present concept can be applied as building block for microfluidic biosensors, which may be disposable. Large liquid transport rates (~150-350 μs$^{-1}$) and velocities (exceeding 400 mm s$^{-1}$) make the substrates suitable for high-throughput pumpless microfluidic devices. The designs are capable of handling small denominations of liquid volume (~1 μL) and repeated disposal of smaller liquid droplets can lead to large (~500 μL) cumulative transport. While the lower volumes are applicable for common microfluidic tasks, the upper volume range is relevant for on-chip liquid storage, or some specialized microfluidic applications that require large volume samples (e.g., in the interrogation well of ultra-wide field fluorescence imaging of undiluted whole-blood samples, which requires volumes ~1 mL). Applicability of the design on metal substrates, on the other hand, make the technique attractive for diverse engineering applications involving a wide range of liquid handling tasks, e.g., rapid chip cooling, water management in fuel cells, or condensate removal in phase change micro-thermal diode.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Method of Preparing a Hydrophobic Coating on a Surface for Wettability Track Provided herein is a method of preparing a wettability track on a substrate, which may be hydrophobic. The hydrophobic substrate may be superhydrophobic. The substrate may be naturally hydrophobic. If the substrate is not naturally hydrophobic, the substrate may be prepared to have a hydrophobic coating. The method may comprise forming a dispersion of titanium dioxide and a fluoroacrylic co-polymer. The titanium dioxide and fluoroacrylic co-polymer may be dispersed in a solvent, such as an alcohol. The dispersion may then be applied to a surface, such as a solid surface. Once applied, the dispersion may form a coating on the surface, which is then dried so as to remove the solvent from the coating. The resultant coating may be hydrophobic. The hydrophobic coating may be superhydrophobic. Hydrophilic patterns, which may be superhydrophilic, may be formed on the coated substrate (i.e. the coated surface of the substrate) by selectively exposing the coated substrate to radiation, such as ultraviolet radiation. The coated surface may be exposed to the radiation through a photomask, for example, to produce the wettability track, which may be a confined wettability track. The wettability track may be wedge-shaped or any desired pattern or combination of patterns to achieve liquid transport.

a. Dispersion

The dispersion may be a two phase system where one phase contains discrete particles of titanium dioxide and fluoroacrylic co-polymer distributed throughout the solvent. The particles constitute the dispersed or internal phase, and the solvent the continuous or external phase. At least a portion of the titanium dioxide and/or fluoroacrylic co-polymer may exist as the discrete particle. Dispersions are possible through the use of certain components that are insoluble in the solvent system. It is desirable that the dispersion remains stable under ambient conditions. Preferred dispersions are stable at room temperature for more than 5 minutes, 30 minutes, 1 hours, 10 hours, 1 day, 30 days, preferably more than 90 days, more preferably for more than 180 days, and most preferably for more than 360 days.

The dispersion may be formed by combining, in any order, titanium dioxide, fluoroacrylic co-polymer, and the solvent. Any of the resultant compositions may be sonicated to produce the dispersion. For example, titanium dioxide and solvent may be combined and sonicated to form a suspension. Once the suspension is formed, the fluoroacrylic co-polymer may be added to it. The entire suspension may then be sonicated to stabilize the suspension and form the dispersion. Alternatively, for example, the titanium dioxide, fluoroacrylic co-polymer, and the solvent may be mixed and then sonicated to form the dispersion. Any sonication method may be used, such as bath or probe sonication. Dispersions may be formed by combining titanium dioxide, fluoroacrylic co-polymer, and the solvent under mechanical mixing at ambient conditions.

The dispersion may comprise from 1 wt % to 25 wt % of fluoroacrylic copolymer. The fluoroacrylic copolymer in water may be added to the aqueous or alcohol solvents, which may or may not yet contain titanium dioxide.

The dispersion may be applied to a substrate and result in a coating that comprises from 5.0 wt % to 95.0 wt % of titanium dioxide. The dispersion may comprise from 1.0 wt % to 25.0 wt % of titanium dioxide. The dispersion may comprise from 5.0 wt % to 12.0 wt %, from 6.0 wt % to 11.0 wt %, from 7.0 wt % to 10.5 wt %, or from 8.0 wt % to 10.0 wt % of titanium dioxide. The dispersion may comprise from 9.0 wt % to 11.0 wt % of titanium dioxide.

The mass ratio of titanium dioxide to fluoroacrylic copolymer may be greater than 1.0. The ratio of titanium dioxide/fluoroacrylic copolymer may be greater than 1.1, 1.2, 1.3, 1.4, 1.5, 1.6, 1.7, 1.8, 1.9, or 2.0, for example. The ratio of titanium dioxide to fluoroacrylic copolymer may be from 1.0 to 4.5, from 1.0 to 4.0, from 1.0 to 3.5, from 1.0 to 3.0, from 1.0 to 2.5, from 1.0 to 2.0, or from 1.0 to 1.5, for example.

The dispersion may comprise from 70 wt % to 97 wt % of alcohol. The dispersion may comprise from 75 wt % to 85 wt %, from 70 wt % to 80 wt %, from 78 wt % to 82 wt %, or from 74 wt % to 84 wt % of alcohol. The dispersion may comprise from 75.0 wt % to 83.3 wt % of alcohol.

(1) Fluoroacrylic Copolymer

The fluoroacrylic copolymer may be any fluoroacrylic copolymer. The fluoroacrylic copolymer may be useful as a matrix to support the titanium dioxide. The fluoroacrylic copolymer may be in the form of a dispersion, such as CAPSTONE® ST-100 (DuPont®).

(2) Titanium Dioxide

The titanium dioxide may be a nanoparticle. The titanium dioxide nanoparticle may be equal to or less than 50 nanometers (nm), for example. The titanium nanoparticle may be equal to or less than 45 nm, equal to or less than 40 nm, equal to or less than 35 nm, equal to or less than 30 nm, equal to or less than 25 nm, equal to or less than 20 nm, equal to or less than 15 nm, equal to or less than 10 nm, for example.

(3) Solvent

The solvent may be any alcohol. The alcohol may be one or more of a monohydric alcohol, an unsaturated aliphatic alcohol, a polyhydric alcohol, and/or an alicyclic alcohol, for example. The monohydric alcohol may be methanol, ethanol, isopropyl alcohol, butyl alcohol, pentanol, and/or hexadecane-1-ol, for example. The polyhydric alcohol may be one or more of ethane-1,2-diol, propane-1,2-diol, propane-1,2,3-triol, butane-1,2,3,4-tetraol, pentane-1,2,3,4,5-pentol, hexane-1,2,3,4,5,6-hexol, and heptane-1,2,3,4,5,6,7-heptol, for example. The unsaturated aliphatic alcohol may be one or more of prop-2-ene-1-ol, 3,7-dimethylocta-2,6-dien-1-ol, and prop-2-in-1-ol, for example. The alicyclic alcohol may be one or more of cyclohexane-1,2,3,4,5,6-hexol, and 2-(2-propyl)-5-methyl-cyclohexane-1-ol, for example.

b. Deposition

The dispersion may be deposited or applied to a surface. The deposition may be performed at standard temperature and pressure, except for various specified heating steps, which may or may not include drying of the coating. The method of deposition may be an aerosol assisted method, dip-coating, and/or spin coating. The aerosol assisted method may be spray deposition or spray casting. The spray casting may be accomplished with an atomizer, for example. A single layer can be deposited on a substrate or multiple layers could be applied. In general, deposition of the one or more layers can be performed by any suitable evaporative coating operation such as dip-coating or drainage, spin-coating, Mayer rod coating, slot coating and other liquid-to-solid coating operations, for example.

c. Substrate/Surface

The dispersion may be applied to any surface of a substrate that can withstand heat and radiative treatment during the formation of regions or patterns or etchings of hydrophilic nature on the dried deposition. Such a substrate may be any metal. The substrate may be steel, aluminum, copper, quartz, glass, fabric, polymer, and/or silicon. The steel may be stainless steel, for example. The polymer may be poly(dimethylsiloxane), for example. The surface may be a flexible substrate, such as a polyethylene terephthalate (PET) film, paper, certain kinds of polymer sheets, for example.

d. Drying

The coating may be dried. The purpose of drying is to remove the solvent from the coating. Once the solvent is removed, the drying step may be complete. The drying may be accomplished by any suitable method for drying including, for example, letting the coating dry at ambient temperature for a period of time, drying the coating in an oven, and/or treating the coating with heat from a heat gun. The coating may be subjected to drying temperatures of from 20° C. to 140° C., from 25° C. to 130° C., from 30° C. to 120° C., from 40° C. to 110° C., from 50° C. to 100° C., from 60° C. to 90° C., from 70° C. to 80° C., for example. The coating may be subjected to a temperature of from 120° C. to 140° C. The coating may be subjected to heat only for a period of time needed to remove the solvent from the coating. For example, the coating may be dried for 5 minutes to 10 hours, from 30 minutes to 9 hours, from 1 hour to 8 hours, from 2 hours to 7 hours, from 3 hours to 6 hours, or from 4 hours to 5 hours, for example. The drying time may depend on the method of drying. The coating may be dried at 60° C. for 4 hours. The coating may be dried at about 23° C. for a time necessary to remove the solvent from the coating.

3. Patterning and Design of Contrast Wettability Domains

The surface of the substrate may be biphilic, whereby two domains of contrast wettability are present. The domains may be in an alternating design, such as alternating parallel strips (striped biphilic patterning). The alternating designs may be interdigitated. The two domains may be any combination of hydrophilic, hydrophobic, superhydrophilic, and superhydrophobic, as long as the two domains have contrasting wettability.

The surface of the substrate may be treated to form one or more hydrophilic regions. For example, the coating may be treated to form one or more of hydrophilic regions, which may be dot-shaped, sphere-shaped, ellipsis-shaped, wedge-shaped, patterns or etchings or tracks, for example, of hydrophilic nature. The hydrophilic region may be in the form of a planar track, or strip, or a wedge-shaped track. The planar track or strip may have a width of from about 300 μm to about 3000 μm.

Figure 17:
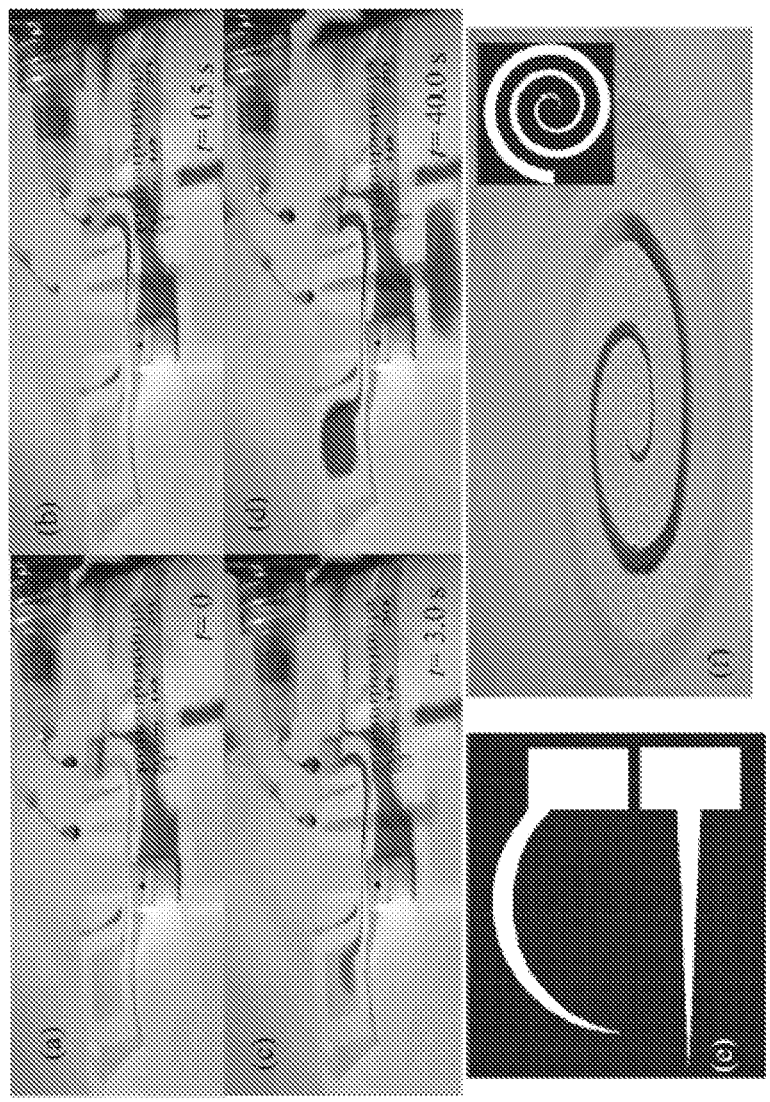
FIG. 17 shows (a)-(e): Combination of a straight (placed horizontally) and a curved (up and down ramp) wedge track designs demonstrating 3-D liquid transport in a "highway overpass" design: (a) before dispensing the liquid droplets, and after dispensing (b, c) the first droplet pair (4.7 $\mu L$ each), (d) 17 droplets (~80 $\mu L$) in the curved track and 28 droplets (130 $\mu L$) on the straight one. (e) The template for droplet overpass design. (f) Liquid transport on a gradually widening spiral superhydrophilic track (inset shows the template design of the photomask).

The wedge-shaped region may be trapezoidal. The wedge-shaped region may have a narrow end and a wide end. For example, a wedge-shaped track may have an end that is 100 μm wide. The other end of the track may be 1 cm wide, for example. The wedge-shaped region may extend from a narrow end to a wider end. The narrow end may be from 10 μm to 500 μm in width. The wider end may be from 500 μm to 2 cm in width. The wedge-shaped track may have a wedge angle ($\theta$) of from 0° to 179°, for example. The wedge-shaped track may have a wedge angle ($\theta$) of 1°, 2°, 3°, 4°, 5°, 6°, 7°, 8°, 9°, 10°, 11°, 12°, 15°, 16°, 17°, 18°, 19°, or 20°, for example. The tracks may form complex designs so as to allow the composition to merge and/or split one or more drops of liquid being transported on the tracks. The tracks may form designs in one or more three-dimensional geometries. The tracks may be straight or curved. For example, the track may spiral as shown in FIG. 17.

The substrate on which the wedge-shaped track is introduced may be inclined. For example, the wedge-shaped region may be an inclined wedge-track. The angle of the incline ($\beta$, where if $\beta=0$, the wedge-track is horizontal), may be any angle at which the liquid moves up or along the plane, for example. The angle of incline may be from 0° (horizontal) to 180° (inverted). The angle of incline may be from 0° (horizontal) to 90° (vertical). The angle of incline may be 45°.

The coating may be treated locally to form the regions or patterns or etchings or tracks of hydrophilic nature.

For the purpose of introducing this wettability transition, radiation may be applied to the coating. The radiation may take on any form. The form of the radiation may be from any radiation source, such as a laser or lamp, for example. The coating may be exposed to radiation treatment for a time on the order of milliseconds to minutes to hours. The coating may be exposed to radiation treatment for from 1 millisecond to 1 hour, for example.

The coating may be exposed to radiation, which may impinge on the surface of the coating. The radiation may pass through a transparent section of a photomask and contact the coated hydrophobic substrate. This application of radiation will locally decrease the hydrophobicity of the area subjected to the heat. The application of the radiation may vary in intensity and duration. The decrease in hydrophobicity may depend on the intensity and duration of the radiation.

The radiation source may provide a wavelength of from 10 nm to 400 nm. The wavelength of the radiation may vary from 50 nm to 350 nm, from 100 nm to 300 nm, from 150 nm to 250 nm, from 200 nm to 225 nm, for example. The wavelength may be 400 nm.

The radiation may be applied only for so long as to produce a hydrophilic area having a contact angle of equal to or less than 15°. The resultant contact angle may be equal to or less than 14°, may be equal to or less than 13°, may be equal to or less than 12°, may be equal to or less than 11°, may be equal to or less than 10°, may be equal to or less than 9°, equal to or less than 8°, equal to or less than 7°, equal to or less than 6°, equal to or less than 5°, equal to or less than 4°, equal to or less than 3°, equal to or less than 2°, or equal to or less than 1°.

4. Pumpless Fluid Transport

Methods for providing pumpless liquid or fluid transport on a substrate are provided herein. The pumpless liquid or fluid transport may be a self-driven transport. A drop of liquid may be applied to an area of the hydrophilic track, which is wettable. For example, the drop of liquid may be applied to a wedge-shaped, superhydrophilic track. The drop of liquid may be applied to the narrow end of the wedge-shaped track, whereby the drop is transported pumplessly toward the wider end of the track.

Alternatively, a liquid droplet may form via condensation on a first domain that is less wettable than the second domain of a patterned (e.g. biphilic) surface. The nucleating droplet may grow and transition across the wettability contrast line. Once across the contrast line, the droplet may be transported away and along the second domain, which is more wettable than the first domain. The more wettable domain may be a track or a strip, for example. As described herein, the track or strip may be wedge-shaped.

The track may be level or inclined. The track may or may not be presuffused or pre-wetted prior to applying the drop of liquid to be transported. The liquid may be transported on a single hydrophilic track, which may be a superhydrophilic track. More than one track may form the hydrophilic area.

The method may comprise applying a drop of liquid fluid to a hydrophilic track on a hydrophobic surface, whereby the drop is transported away from the point of application. The hydrophilic track may be confined by the hydrophobic surface. The hydrophilic track may be superhydrophilic and/or the hydrophobic surface may be superhydrophobic. The track may be a wedge-shaped track and the drop of liquid is transported toward the wider end of the wedge-shaped track. The track may be presuffused (pre-wetted) prior to the application of the drop of liquid fluid. The track may direct the merging of two or more droplets of liquid. The track may direct the splitting of one or more droplets of liquid.

The track may be formed from one or more geometrical hydrophilic shapes produced by the radiation or another wettability patterning technique. The shapes may be selected from the group consisting of dots, spheres, wedges, ellipses, squares, rectangles, trapezoids, and combinations thereof. The track or tracks on the substrate may form a pattern. More than one hydrophilic track may be produced on the surface. The resultant wettability track or tracks on the substrate may form a shape, such as a spiral. The resultant wettability track or tracks on the substrate may form a pattern. The pattern or shape may direct the merging of two or more droplets of liquid. The pattern or shape may direct the splitting of one or more droplets of liquid.

The liquid may be transported at a volume flow rate of from 1 µL s$^{-1}$ to 600 µL s$^{-1}$, from 50 µL s$^{-1}$ to 450 µL s$^{-1}$, from 100 µL s$^{-1}$ to 400 µL s$^{-1}$, from 200 µL s$^{-1}$ to 350 µL s$^{-1}$, or from 250 µL s$^{-1}$ to 300 µL s$^{-1}$, for example. The liquid may be transported at a volume flow rate of about 350 µL s$^{-1}$. The liquid may be transported without back-flow of the liquid on the track. The volume flow rate of the liquid may exceed 500 µL s$^{-1}$. The volume flow rate may be between 1 ml s to 3 ml s, for example. The volume flow rate may be 1 ml s$^{-1}$, 2 ml s$^{-1}$, or 3 ml s$^{-1}$.

The transport of the liquid may take place in the form of a wetting front or a wetting front followed by an advancing liquid bulge. The transport speed may be from 1 mm/s to 500 mm/s, from 50 mm/s to 450 mm/s, from 100 mm/s to 400 mm/s, from 150 mm/s to 350 mm/s, from 200 mm/s to 300 mm/s, or from 250 mm/s to 275 mm/s. The transport speed of the liquid may exceed 400 mm/s.

The volume of the drop of liquid applied to the track may be from 0.5 µL to 1 ml, from 1 µL to 900 ml, from 25 µL to 850 µL, from 100 µL to 750 µL, from 200 µL to 600 µL, from 300 µL to 500 µL, from 400 µL to 450 µL, from 1 µL to 25 µL, from 1 µL to 20 µL, from 1 µL to 15 µL, from 1 µL to 10 µL, or from 1 µL to 5 µL. The volume of the drop of liquid applied to the track may be from 4 µL to 5 µL.

The liquid to be transported may be any liquid. For example, the liquid may be water or alcohol, for example. The liquid may be a refrigerant (as long as the corresponding surface features both wettable and non-wettable domains with respect to this specific liquid). The liquid may be a biological sample. The biological sample may be blood, plasma, urine, or any tissue dissolved or dispersed in a liquid or solvent. The liquid may be any biochemical agent dissolved or dispersed in a liquid solvent. The biochemical agents may include but are not limited to biomarkers, proteins, nucleic acids, pathogens, drugs, and/or toxins. The liquid may be oil or a liquid propellant. The liquid may have a high surface tension, whereby a higher surface tension corresponds to a faster transport speed. The liquid may be aqueous or non-aqueous.

5. Condensing Environment

The herein described compositions may be exposed to a vapor condensing environment. The condensing environment results in the change in the state of vapor to liquid when in contact with a surface of the composition. The condensing environment may have a relative humidity of from about 10% to about 100%. The condensing environment may have a temperature of from about 5° C. to about 200° C. The condensing environment may have a temperature of from about 5° C. to about 200° C. The condensing condition may be stagnant or flowing. The orientation of condensing surface with gravity can be horizontal, inverted, vertical, or any orientation angel ranging from 00 to 900, for example. The condensing liquid may be any aqueous or non-aqueous liquid.

6. Compositions

Compositions or articles comprising the hydrophobic or binary/biphilic coatings are provided herein. The compositions may be, for example, an open substrate, such as a planar chip. The composition may be a microfluidic device. Such compositions may be useful for guiding and confining mobile droplets as desired on the open substrate. Microfluidic devices require very accurate control of fluid motion. Often, this is achieved by moving the fluid slowly enough that individual "layers" of fluid move parallel to one another in a condition known as "laminar flow." Microchip fluidic systems may be used to electrokinetically transport fluids. Examples of this technique can be found in U.S. Pat. No. 6,046,056 issued Apr. 4, 2000; U.S. Pat. No. 6,045,676 issued Apr. 4, 2000; U.S. Pat. No. 6,042,710 issued Mar. 28, 2000; and U.S. Pat. No. 6,033,546 issued Mar. 7, 2000. The devices employed in microchip fluidic systems may also be referred to as microchip capillary devices, microfabricated devices, and microfluidic devices. Such devices may be made from silicon, quartz, glass or polymers such as poly (dimethylsiloxane), for example. The device may be a miniaturized capillary system. In addition, such devices may be used as point of care biological marker detection devices. The devices may integrate and automate one or more of blood sample preparation, cell sorting and enrichment by microcytometry, antigen marker or biomarker analysis, DNA sequence analysis, and gene expression analysis.

The identification of a biomarker may be for the purpose of early detection and diagnosis of a disease, for example cancer. Biomarkers may be protein molecules that can be measured in blood, other body fluids, and tissues to assess the presence or state of a disease. Assaying for the presence and/or level of certain biomarkers in body fluids, miniaturized immunoassays that make use of microfluidics have become an important analysis technique. Microfluidic chips having hydrophilic/hydrophobic designs and tracks that are manufactured by the methods disclosed herein, may be used to assay for levels of hormones, disease markers, response to infection with bacteria and viruses, or monitor the evolution of a disease and/or test for medication levels.

The hydrophilic designs may be capable of handling small denominations of liquid volume. Repeated disposal of smaller liquid droplets may lead to large cumulative transport. The compositions may be components for dehumidifiers, components for condensation apparatuses, components for distillation apparatuses, components for boiling applications, components for water management in fuel cells, components for direct liquid impingement, electronics cooling, components for handling liquid propellants under reduced gravity, bio-medical and microfluidic devices, protective layers for semiconductors, anti-corrosion coatings, films on windows, home appliances, roofs, greenhouses, sun rooms, swimming pool enclosures, and the like. The compositions may be of particular utility in the manufacture of pipes, such as heat exchanger pipes, for example.

The surface of any composition, article, or substrate described herein may include two domains of contrast wettability (e.g. biphilic). The domains may be in an alternating design, such as alternating parallel strips (striped biphilic patterning). The alternating designs may be interdigitated. The two domains may be any combination of hydrophilic, hydrophobic, superhydrophilic, and superhydrophobic, as long as the two domains have contrasting wettability.

The surface of the composition, article, or substrate may be treated to form one or more hydrophilic regions. For example, the coating may be treated to form one or more of hydrophilic regions, which may be dot-shaped, sphere-shaped, ellipsis-shaped, wedge-shaped, patterns or etchings or tracks, for example, of hydrophilic nature. The hydrophilic region may be in the form of a planar track, or strip, or a wedge-shaped track. The planar track or strip may have a width of from about 300 µm to about 3000 µm.

Directed motion of droplets may be useful in the creation of container-less, surface-tension confined fluidic devices that are non-fouling, easy to clean, and allow transport of highly concentrated fluids with no loss to the walls. The ability to coalesce drops also can provide the means to perform highly controlled reactions upstream of the fluidic analysis and has implications also for flow cytometry.

As described above, the herein described dispersions may be useful as compositions to be applied to any surface than can withstand the heat treatment step. The substrate may be a metal, such as steel or aluminum. The metal may be polished. The metal may have a mirror finish. The substrate may be paper, copper, quartz, glass, plastic, fabric, and/or silicon for example. Again, the applicability of the herein described designs on metal substrates make the herein described methods attractive for diverse engineering applications involving a wide range of liquid handling tasks. Such tasks may include rapid electric chip cooling, water management in fuel cells, and/or condensate removal in phase change heat transfer devices, which may include heat pipes, fins, and micro-thermal diodes. The dispersion may be useful for any of the above-described applications.

The present invention has multiple aspects, illustrated by the following non-limiting examples.

EXAMPLES

Example 1

Materials and Methods Used in Examples 2-10

Materials: The chemicals used comprise a fluoroacrylic copolymer dispersion (PMC) manufactured by DuPont (20 wt. % in water; Capstone® ST-100), titanium (IV) dioxide nanoparticles (anatase, <25 nm, 99.7% trace, Sigma Aldrich) and ethanol (~100% wt., Decon Labs). The following substrates were used: mirror-finish aluminum plate (multipurpose polished aluminum alloy 6061, 2 mm thick, McMaster Carr), transparency film for laser copiers (cross-linked polyethylene terephthalate (PET), PP2500, 3M), and white photocopier paper (80 g m$^{-2}$, Paper One). The PMC copolymer serves as the primary component of the superhydrophobic surface. The $TiO_2$ nanoparticles impart the required micro- and nano-scale roughness, and promote hydrophilicity through well-known mechanisms and possible photocatalytic degradation of hydrophobic chemistries upon exposure to UV radiation. All of the above materials were obtained off-the-shelf, and are readily available in the marketplace.

Methods: We used a facile and scalable approach to fabricate samples that juxtapose wettable and non-wettable spatial domains of various shapes and sizes. A typical example for synthesizing such wettability patterned coatings is presented. First, a dispersion—containing the hydrophobic PMC copolymer, $TiO_2$ nanoparticles, and ethanol—was prepared and subsequently spray deposited onto the substrates in order to generate a superhydrophobic surface. To synthesize the dispersion, a suspension of $TiO_2$ and ethanol was first formed. 1.5 g of $TiO_2$ was added to 14 g of ethanol, and was then probe sonicated (750 W, 13 mm probe diameter, 40% amplitude, 20 kHz frequency, Sonics and Materials Inc., Model VCX-750) by supplying 1000 J of energy. Next, 2.5 g of PMC solution (20 wt. % in water) was added and shaken mechanically at room temperature to form a stable dispersion. The above solution was sprayed on three different types of substrates (mirror-finish aluminum, PET films, and paper) using an airbrush (VL siphon feed, 0.73 mm spray nozzle, at 276 kPa (gage) air pressure, Paasch) to form a uniform coating. The spray-coated samples were then dried in a preheated oven at 60° C. for 4 hours, ultimately forming a superhydrophobic surface suitable for wettability patterning. Superhydrophilic patterns were formed on this superhydrophobic surface through selectively exposing the coated substrate to UV radiation (Dymax™ 5000 EC, 400 W, 390 nm UV Source) through a photomask (a transparency film with printed black negative patterns using a common household laser printer) for 30 minutes (see FIG. 1). The UV light passed through the transparent (unprinted)

section of the mask and struck the coated superhydrophobic substrate. The presence of $TiO_2$ in the composite promoted photocatalytic conversion of the exposed domains, rendering them superhydrophilic. Complex pattern designs with features as fine as 200 μm were obtained using this photomasking technique.

Scanning electron microscopy (Hitachi S-3000N) was performed for visualizing the roughness features of the spray-deposited surface. Experiments were conducted by first mounting the substrate on a horizontal micro stage. A high-speed camera (Redlake Motion Pro, mounted with Navitar TV ZOOM 7000 or OPTEM ZOOM 100 lens) was used to capture the rapid events, such as liquid bridging, de-bridging and droplet volume splitting. The substrates were illuminated by a cool light source (FOSTEC, 8375). The real-time fluid transport features were recorded using a standard DSLR (Canon Rebel Ti) camera mounted with a macro telephoto zoom lens (Sigma 70-300 mm). The water drops (~4.7 μL) were dispensed with a syringe pump (Cole-Palmer, 74900) through a 100 μm inner diameter needle (Nordson EFD, 32GA GP). The needle was strategically placed above the substrate such that the drops fell on the desired location at low speed, and the inertial effects remained negligible as compared to capillary force.

Example 2

Figure 10:
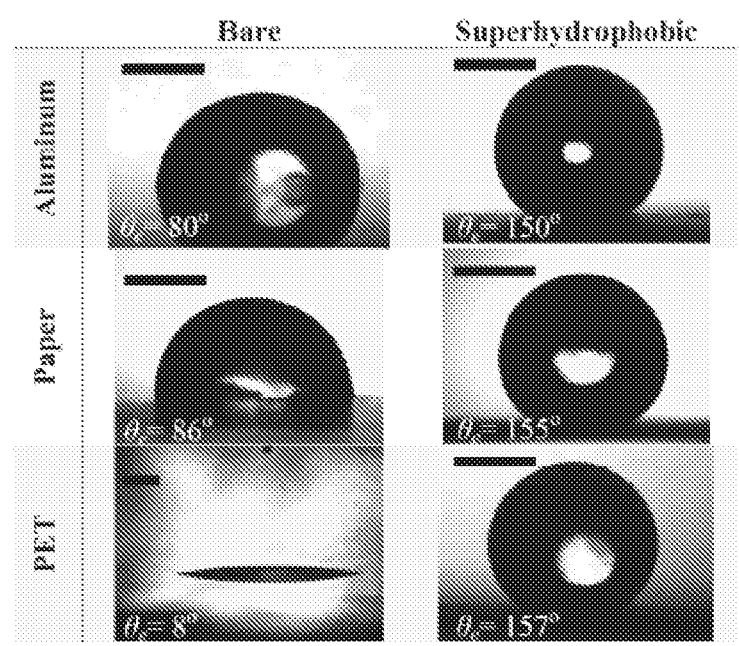
FIG. 10 shows sessile droplets on the bare substrate (left) and superhydrophobic sections (right) of aluminum, paper and PET substrates. This figure shows one typical image for each substrate taken from several runs used to obtain the $\theta_e$ data listed in Table 1. Each scale bar denotes 1 mm.

UV-Exposed Superhydrophilic Tracks and Liquid Transport Along a Wedge-Shaped Track Scanning Electron Microscopy images of the coated substrate (see FIG. 1) show the presence of multiscale roughness features ranging from a few hundreds of nanometers to a few tens of microns, as produced by the $TiO_2$ nanoparticles. The parts of the substrate that were not exposed to the UV radiation retained their hydrophobicity. The average equilibrium contact angle values (computed from at least 10 sets of data for each type of surface) are listed in Table 1, while sample images of sessile drops on each substrate are given in FIG. 10. As-received samples of aluminum, paper and PET films exhibited average sessile contact angles of 78.2±20, 85.5±4, and 8.5±20, respectively. The micron and submicron features of the coated surface did not differ with the nature of substrate (e.g., Al plate, PET film or paper). Consequently, the superhydrophobic sections of the substrates exhibited contact angle values ranging from 151 to 156 at room temperature irrespective of the substrate (see Table 1). The UV-exposed superhydrophilic tracks, on the other hand, exhibited contact angles lower than 3°, the exact value of which could not be measured. For paper substrates, prolonged exposure to water on the superhydrophilic regions produced capillary imbibition through the substrate itself, thereby making CA measurements difficult.

TABLE 1

Equilibrium Contact Angle ($\theta_E$)* on Substrates (*Contact angle data evaluated from sets of at least 10 readings; ** Contact angles were too low to measure).

|  | Uncoated Substrate | Coated Substrate (Hydrophobic Part) | Coated Substrate (Hydrophilic Part) |
| --- | --- | --- | --- |
| Aluminum | 78.2 ± 2° | 151.2 ± 2.3° | ** |
| Paper | 85.5 ± 4° | 154.5 ± 2° | ** |
| PET Film | 8.5 ± 2° | 156 ± 3° | ** |

Figure 2:
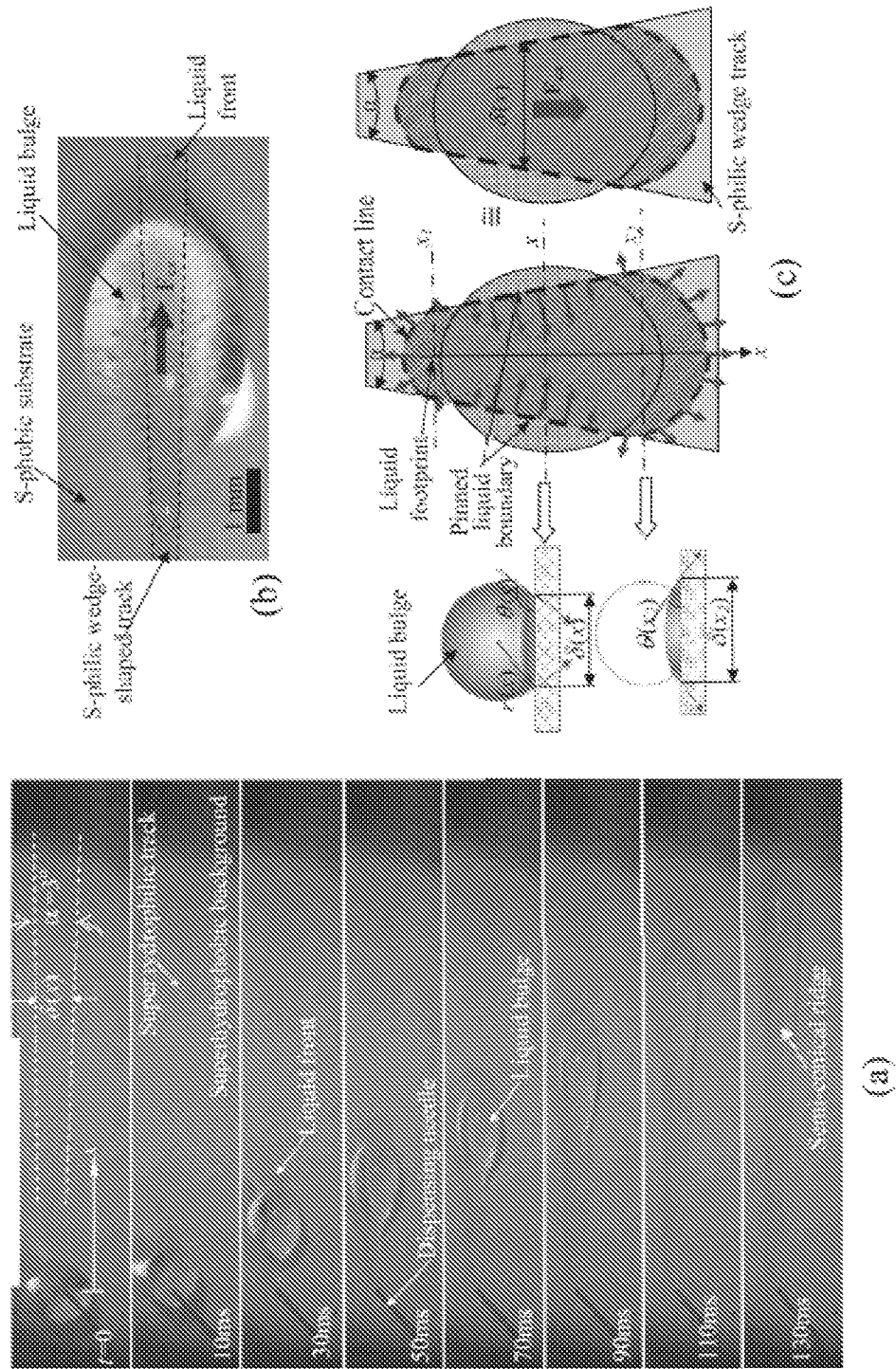
FIG. 2 shows (a) time-lapsed images of liquid transport through the wedge-shaped superhydrophilic track on a horizontal aluminum substrate. The white scale bar at the top denotes 10 mm. (b) Top view showing morphology of the liquid bulge, approximated as an ellipsoid of finite footprint on the wedge-shaped superhydrophilic track, moving along the track; (c) force diagram depicting the origin of the driving capillary force on the liquid bulge.

Different shapes of superhydrophilic patterns have been examined. As the simplest building block of such patterns, a wedge-shaped superhydrophilic track (akin to a long and narrow tapered path) with wedge angle=3° was initially chosen. FIG. 2(a) shows time-lapsed images of liquid transport of a 4.7 μL droplet deposited at the narrow (left) end of a wedge track on a horizontal Al substrate (the photomask actually produced a trapezoidal shape; the droplet was deposited ~1 mm to the right from its narrowest edge, which was ~770 μm wide). The superhydrophilic track width where the droplet was deposited is approximately 820 μm, which is significantly narrower than the droplet diameter (~2 mm). Therefore, the liquid spreading in the transverse direction (i.e., towards the hydrophobic regions on either side of the track) was constricted by the wedge boundary. After the droplet came in contact with the track (t=0 snapshot in FIG. 2), a rapidly advancing film front was observed to propagate ahead of the droplet towards the wider end of the track. This was driven by hemiwicking through the microscale roughness features on the superhydrophilic track. The bulk of the fluid trailed behind the propagating front in the form of a liquid bulge with a progressive axial elongation. As the liquid front advanced further along the wedge track, the bulge disappeared gradually and the liquid took the shape of a semi-conical rivulet. Prior studies have been performed on wetting morphologies of static liquid volumes confined laterally on narrow superhydrophilic tracks patterned on superhydrophobic background. The shape of such liquid accumulation on rectangular tracks may depend on the ratio $\Omega/\delta^3$ (where $\Omega$ denotes the liquid volume and $\delta$ the superhydrophilic track width). Below a critical value of $\Omega/\delta^3$, the liquid assumes a semi-cylindrical shape (elongated along the track and confined by the wettability contrast lines at the two sides of the tracks). This critical value depends on the equilibrium contact angles on the superhydrophobic and superhydrophilic domains ($\theta_{Sphobic}$ and $\theta_{Sphilic}$). The liquid volume in FIG. 2 was in a dynamic state. A similar bulge-like morphology was observed close to the point of deposition (i.e., x~0) where $\Omega/[\delta(x)]^3=4.7/(0.82)^3\approx8.52$. The local track width increases linearly with the distance x along the wedge-shaped track. Therefore, for a given volume of the deposited droplet $\Omega/[\delta(x)]^3$, decreases with increasing x. For the image sequence in FIG. 2(a), the liquid bulge morphology was observed up to x=14.5 mm (where $\delta$=1.55 mm), corresponding to $\Omega/[\delta(x)]^3\approx1.26$. This can be reckoned as the critical value for the track considered here. The subcritical morphology here is a bounded semi-conical shape.

The liquid along the wedge-shaped track in FIG. 2 is driven by the unbalanced capillary forces in the lengthwise direction, which push the droplet from a smaller wettable footprint (left) to a larger one (right). Over the initial length of 15 mm, the liquid bulge recorded an average velocity (measured as the displacement rate of the largest girth of the elongated liquid volume traveling along the track) of 110 mm s$^{-1}$. After the first droplet passed, the superhydrophilic channel became wet (presuffused). When an identical-size droplet was deposited at the narrow end of the presuffused track, both the liquid bulge and the propagating front behaved in a similar manner, but they exhibited even higher velocity (~300 mm s$^{-1}$) in the first 15 mm.

The initial advancement of the liquid film on the track is akin to hemiwicking of liquid on a textured superhydrophilic track. However, the liquid bulge motion is strongly influenced by the Laplace pressure differential between its front and back. FIG. 2(b) shows a close-up of the liquid bulge as it traveled from left to right along the wedge-shaped superhydrophilic track. The elongated droplet has a footprint that leads at the front end and trails at the rear side of the bulk with very small contact angles (due to near-complete wetting of the superhydrophilic track). The apparent contact angle θ(x) of the liquid bulge along the two straight edges of the footprint (where the liquid contact line is pinned) does not follow Young's equation; rather it is governed by the local track width and the liquid volume contained per unit length at that particular location of the track. Theoretically, this angle should be less than $\theta_{Sphobic}$ and greater than $\theta_{Sphilic}$, and would vary along the track length x. The net capillary force $F_{cx}$ on the droplet may be obtained by taking the axial derivative of the total surface energy of the system, namely $$F_{cx} = -\frac{d}{dx}[\gamma_{LS}A_{LS} + \gamma_{LG}A_{LG} + \gamma_{SG}A_{SG}], \quad (1)$$

where γ denotes the surface energy per unit interface area between the solid (S), liquid (L) and gas (G), and A is the corresponding surface area. Intuitively, the liquid has a propensity to move forward, as that leads to wetting of a larger area of the superhydrophilic track, resulting in a net lowering of the surface energy in the positive x direction. As seen in FIG. 2(c), the liquid bulge experiences surface tension forces along the leading and trailing boundaries of the liquid footprint, and also along the pinned sidelines. Clearly, the leading edge has a larger length than the trailing one due to the wedge shape of the track. Also, the top view of the droplet in FIG. 2(b) indicates that θ>90° for most of the section of the liquid bulge that touches the pinned sidelines. Thus, along these axially diverging contact lines, the net component of surface force acts along the positive x direction. This propels the liquid droplet, a phenomenon not observed on a straight fixed-width hydrophilic track. The local Laplace pressure at any section of the liquid bulge is $\sim\gamma_{LG}/r(x)$ where the local curvature of the liquid $r(x) \approx \delta(x)/[2 \sin\theta(x)]$. Both θ(x) and δ(x) vary along the length of the track (for small wedge angles, δ(x) is proportional to the wedge angle α). Assuming a representative average contact angle $\theta_{avg}$ over the length of the bulge, the net axial Laplace pressure gradient in the liquid bulge can be estimated as $$\frac{dP}{dx} \sim -\frac{d}{dx}\left[\frac{\gamma_{LG}}{r(x)}\right] \sim -\gamma_{LG}\frac{d}{d\delta(x)}\left[\frac{2\sin\theta(x)}{\delta(x)}\right]\frac{d\delta(x)}{dx} \sim 2\gamma_{LG}\sin\theta_{avg}\frac{1}{\delta(x)^2}\alpha. \quad (2)$$

Figure 3:
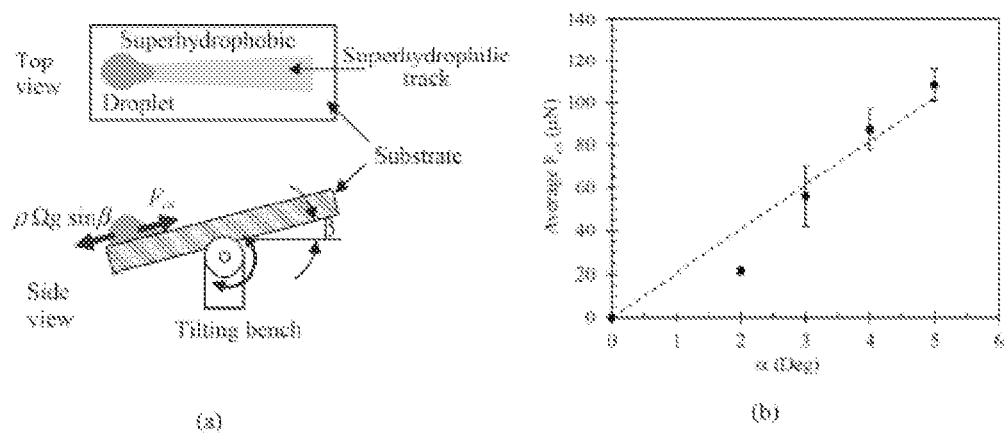
FIG. 3 shows (a) arrangement for measurement of capillary force $F_{ex}$ at the narrow end of the wedge at the onset of droplet motion. (b) Variation of $F_{ex}$ with the wedge angle α (error bar shows the standard deviation in readings due to variability in droplet volume).

This pressure gradient is responsible for driving the droplet to the wider portions of the wedge track. Equation (2) indicates that the capillary pressure gradient is proportional to the wedge angle α and inversely proportional to the square of local track width δ(x). However, evaluating the magnitude of the capillary force from this expression requires a priori knowledge of how the angle θ(x) varies with x, which requires computational analysis. A separate experiment was therefore carried out (see FIG. 3(a)) under a static scenario to calculate the capillary force on the droplet at the onset of the motion. The substrate was mounted on a tilt platform with a large enough inclination so that a droplet placed at the narrow end of the presuffused wedge did not move up. The tilt angle β was gradually reduced until the capillary force became comparable to the in-plane component of the droplet weight, so that the droplet moved up the plane. For a known droplet volume Ω (the test was repeated with different volumes of dispensed droplets) and β measured from the experiment, the capillary force (at the narrow end of the wedge-track) can therefore be calculated as $$F_{cx} = \rho\Omega g \sin\beta. \quad (3)$$

FIG. 3(b) shows the variation of capillary force on the droplets with the wedge angle. Each data point represents about 100 readings taken with dispensed droplet volumes ranging from 4.7 μL to 23.5 μL (the readings of β, and hence the $F_{ex}$ did not vary much with Ω while the error bars represent the standard deviation in reading. Clearly, the linear nature of the plot of $F_{cx}$ against α shows conformity to Eq. (2). The capillary force for the case shown in FIG. 2 (i.e., α=3°) is found to be approximately 56.3 μN, which would, in absence of any restrictive forces produce an instantaneous acceleration of 12 m s$^{-2}$ for a 4.7 μL droplet. The observed acceleration on a horizontal substrate could differ from this value since the actual bulge volume is slightly less than 4.7 μL (part of the liquid spread by hemiwicking). Also, in reality, the motion of the liquid bulge is resisted by contact angle hysteresis (CAH) between its advancing and receding fronts, as well as viscous forces. The effects of the first two factors (loss of liquid from the bulge due to hemiwicking, and the restrictive force due to CAH) have competing influence on the droplet acceleration, while the viscous force on the droplet at the onset of its motion is negligible. Later in this section, we shall see that the predicted value of acceleration indeed matched closely with the observed initial acceleration of the liquid bulge on a presuffused track.

Figure 12:
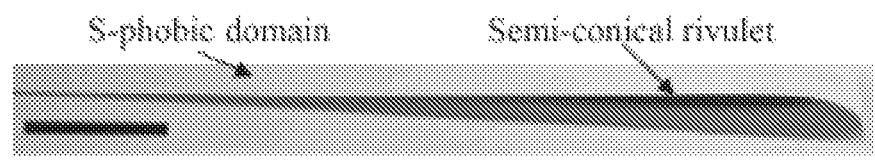
FIG. 12 shows an image of the liquid accumulated after approximately 235 mL of water (dyed for better visualization) were dispensed at the left end of the track. Scale bar denotes 10 mm.

At the far downstream portion of the wedge track, the contact angles at the pinned sidelines may become less than 90°, thus having a contribution that resists the forward motion of the bulk liquid (see FIG. 2(c)). This may lead to a flagging $F_{cx}$ at the downstream portion of the tracks, forcing the droplet transport to cease. However, for the geometry considered in FIG. 2, and the liquid volumes dispensed herein, sustained forward movement of the droplets persisted until the droplets reached the wide edge of the track (travel path ~25 mm). Subsequent droplets (deposited afterwards at the same location) also exhibited similar behavior on the presuffused track, although these moved faster. The track kept pumping the liquid from the narrower end and accumulating it at the wider end in the form of a growing bulge (the latter happened if the accumulated volume exceeds the threshold value discussed before). A separate study on a 60 mm long wedge-shaped track having α=4° showed that the track was able to hold 235 μL of water in a rivulet shape before bulging out at its wider end (see FIG. 12).

Figure 4:
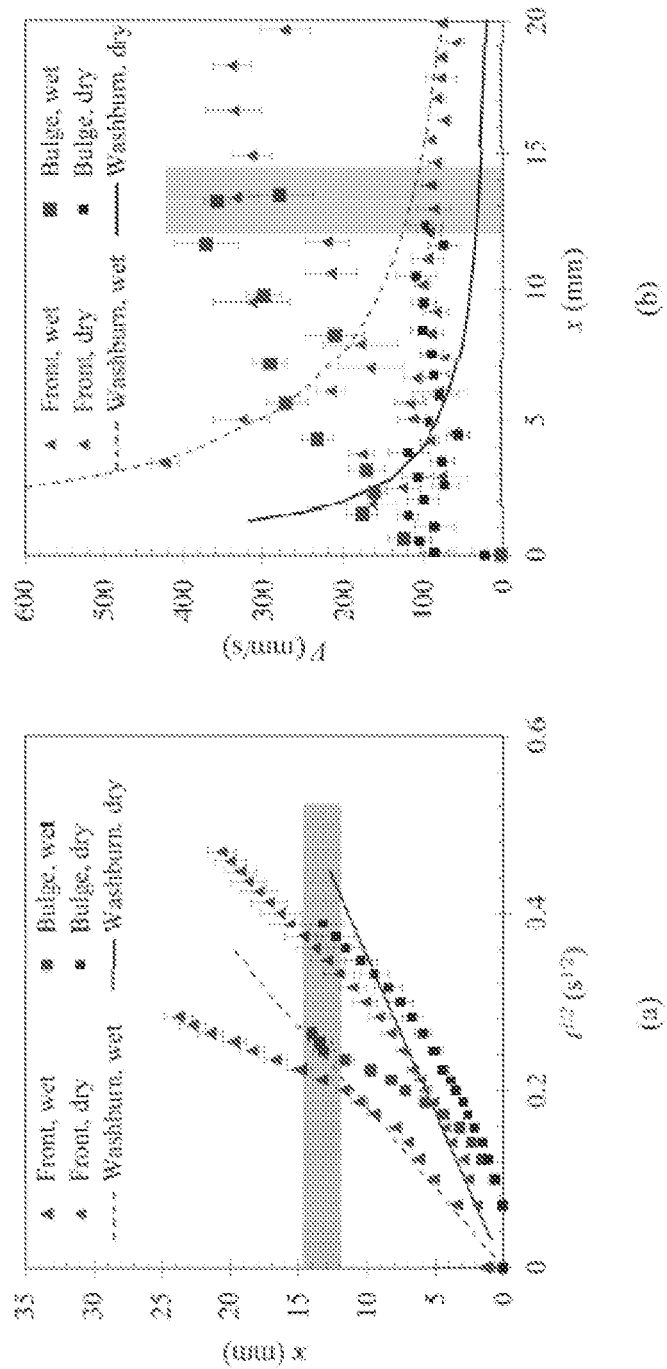
FIG. 4 corresponds to transport of the liquid front and the liquid bulge along a wedge shaped track with α=3° (see FIG. 2a). (a) Distance x from the dispensing location as a function of $t^{1/2}$, and (b) velocity as function of position x along the track. Comparison of the experimental data (symbols) with the Washburn model for wetting behavior (continuous curves) is also made. The gray bar denotes the spatial region in which the "bulge" volume shape transformed to the spreadout rivulet shape.

FIG. 4 shows (a) the displacement-time (on x-t$^{1/2}$ axes) and (b) the velocity-displacement profiles of the liquid front and the bulge on a dry track and on a presuffused track. Each plot represents readings averaged over at least six independent runs, while the error bars show the standard deviation. As seen from FIG. 4, the liquid front begins to spread along the dry track at a high speed (~165 mm s$^{-1}$ at x=1.9 mm) but it gradually slows down (~90 mm s$^{-1}$ at x=7 mm) as the liquid film spreads down the track. This propagation can be attributed to the capillary wetting of the textured philic track by the liquid. Typical capillary wetting would exhibit the Washburn profiles for displacement-time and velocity-displacement plots, following $x=\sqrt{\gamma_{LG}d_{pore}t/4\mu}$ (straight line on x-t$^{1/2}$ plot), and $V \sim \gamma_{LG}d_{pore}/\mu x$ (rectangular hyperbola on V-x plot), respectively. The hemiwicking displacement and velocities for Washburn flow are also plotted in FIG. 4 for water ($\gamma_{LG}$=72.1 mN m$^{-1}$, dynamic viscosity μ=0.89 mPa s), assuming an estimated mean surface feature size (created by the TiO$_2$ particles) $d_{pore}$=40 nm. Although pore size was used as a fitting parameter, the optimal value is consistent with the size of aggregated TiO$_2$ particles that create the surface texture. The observed displacement plot for the liquid front showed agreement with the Washburn profile for approximately the first 5 mm of travel (see FIG. 4(a)), and exceeded the latter significantly in the downstream region. The liquid bulge, on the other hand, exhibits a relatively sluggish start due to its inertia, but it soon speeds up to closely follow up the liquid front. Beyond x~7 mm the liquid bulge is found to move at nearly the same velocity with the front, trailing it by 2 mm, until the bulge shape disappears. At this stage, the liquid bulge following the hemiwicking front acts as a "source" that offers the driving potential for the liquid front to propagate further ahead. This eventually causes the liquid front's velocity to exceed that predicted from the Washburn equation (FIG. 4(b)).

Figure 13:
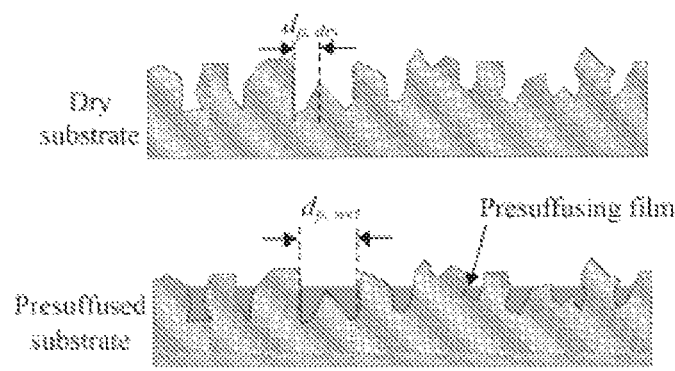
FIG. 13 shows the effect of presuffusing on liquid mobility: for a dry track (top) the smaller surface features (characteristic dimension $d_{p,\ dry}$) limit the liquid hemiwicking speed. For a presuffused track (bottom), the narrower crevices of the tracks are submerged, and the hemiwicking speed is limited by the relatively larger features ($d_{p,\ wet}$) of the exposed surface roughness.

On a presuffused track, the effective capillary pore diameter ($d_{pore}$) is larger than that exhibited by the dry tracks since the finer microstructure features on the surface remain submerged, leaving only larger surface "apex" features to influence hemiwicking (see FIG. 13). Thus, the initial velocity of the hemiwicking front on a presuffused track should be much larger. Indeed, as seen in FIG. 4, the liquid front on a presuffused tack recorded an initial velocity ~424 mm/s, which approximates a Washburn velocity profile corresponding to $d_{pore}$=150 μm (optimal value obtained by fitting the experimental data). As in the case of a dry track, the liquid bulge on a presuffused track also accelerated from rest, and gradually moved faster. The acceleration of the liquid bulge at the inception of the droplet motion was found to be $dV/dt|_{t=0}$=12.3 m s$^{-2}$ (see FIG. 14). This is in excellent agreement with the acceleration (12 m s$^{-2}$) evaluated from the capillary force diagram (FIG. 3(b)). Beyond x~6 mm, the liquid bulge velocity exceeded the velocity of the front, but was not able to catch up within the available track length. The front velocity also picked up speed as it received better "feed" from the liquid bulge trailing right behind it. FIG. 4 clearly indicates that the motion of the liquid front through the wedge-shaped superhydrophilic track follows the Washburn behavior only in the first few millimeters of the track length beyond which the advancing velocity is significantly bolstered by the liquid bulge trailing behind the propagating meniscus. Similar behavior was also observed when water droplets containing 10% ethanol (by wt.) were transported on the same wedge-track, but the average velocity was lower (~83% of that observed with pure water) due to the lower surface tension (47.5 mN m$^{-1}$) and higher viscosity (1.21 mPa-s) of ethanol-water mixture.

Example 3

Liquid Transport Using Complex Patterns

Figure 5:
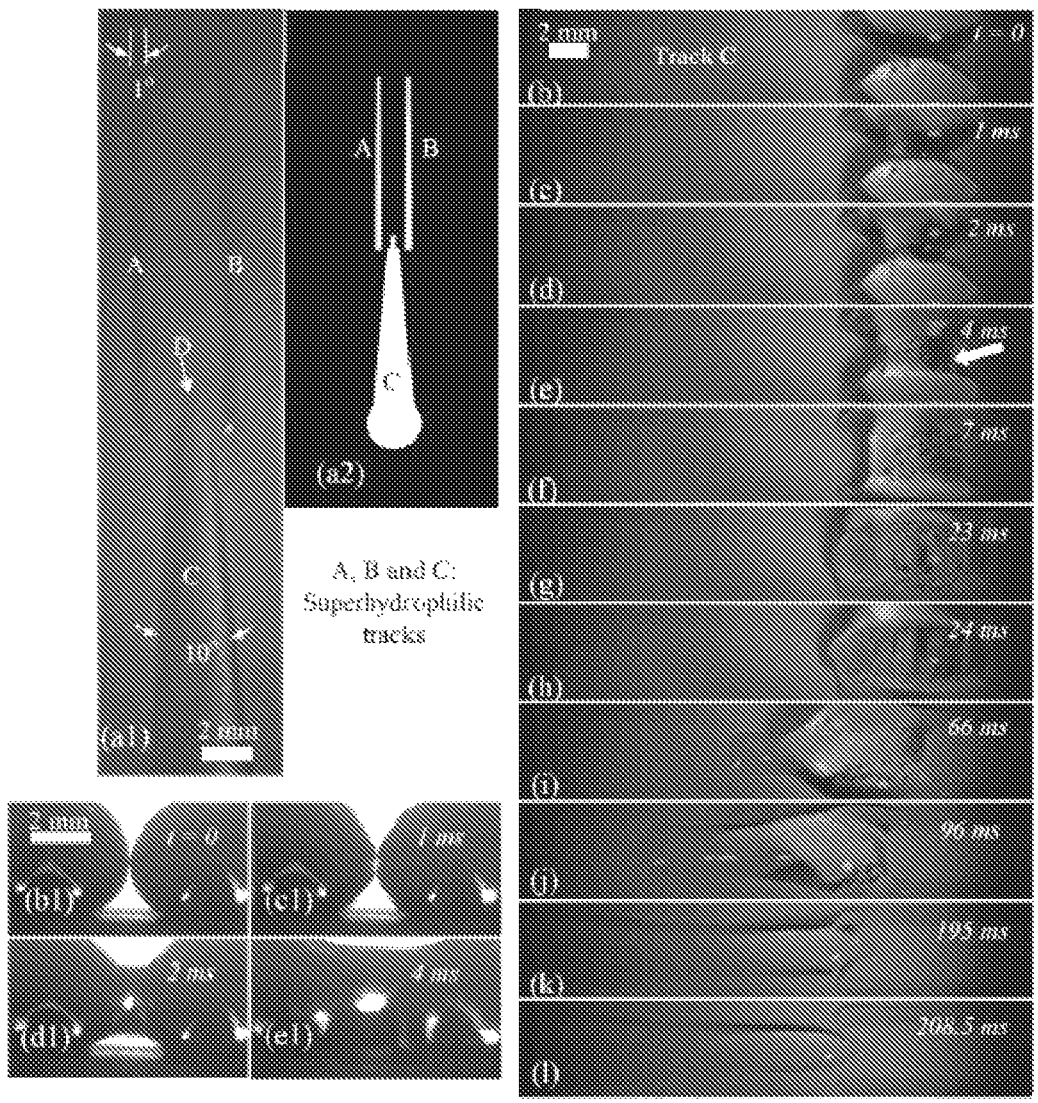
FIG. 5 shows a patterned Al substrate (a1) and the mask (a2) used for demonstrating a multi-step functional surface device capable of performing pumpless liquid bridging and draining Snapshots of events on the liquid bridge circuit: (b, b1) Liquid bulges at the wider ends of tracks A and B just before a liquid bridging event; (c, c1) onset of liquid bridging, (d-f) progression of liquid bridge formation; (g-h) liquid bridge touches the tongue D of track C; (i-k) progression of liquid pumping; (l) de-bridging at the end of pumping. Starting from the onset of the liquid bridge touching track D (frame (g)) to the de-bridged state (frame (l)), this procedure achieves an average pumping rate of 357 $\mu L\ s^{-1}$. (b1)-(e1): End views of the bridge formation and growth events (top views in (b)-(e)) as seen from the downstream delivery side of the device.
Figure 15:
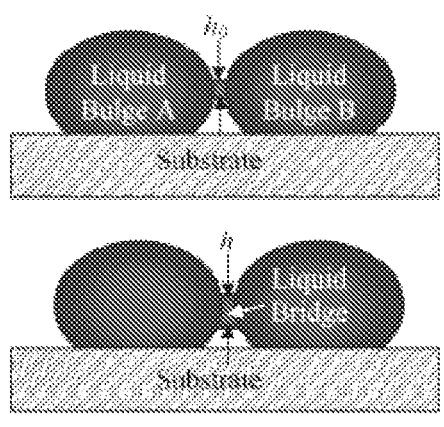
FIG. 15 shows the growth of the capillary bridge thickness (normalized with $h_0$, the initial bridge thickness) as measured from FIGS. 5(b1-e1) as a function of time. The bridge height exhibits a linear dependence with $t^{1/2}$.
Figure 15:
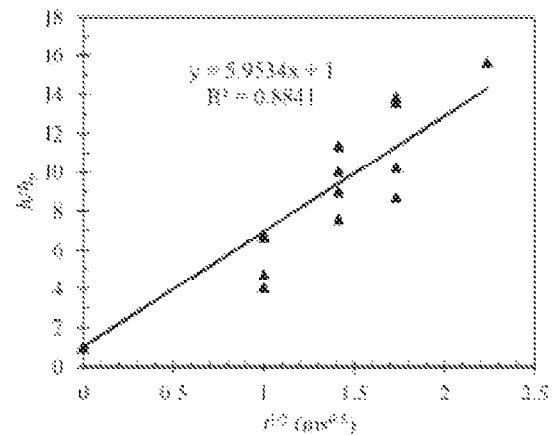

Droplet metering, merging and rapid transport. Having established the pumping capability of the individual wedge-shaped tracks, more complicated surface patterns comprising of these tracks were designed to demonstrate multi-step functionalities. It is apparent from the previous section that the wedge-shaped tracks transport the liquid towards the wider end either in the form of a bulge (early) or a semi-conical rivulet (late). If two such tracks are laid parallel to each other, and the $\Omega/\delta^3$ ratio for the track (Acing the track width at the wider end) is large enough to favor the "bulge morphology," it is possible to generate two adjacent liquid bulges with the potential to interact with one another towards certain functionalities. For example, if the intervening space between the adjacent tracks is comparable to the lateral width of each liquid bulge, the menisci of the accumulated liquids at the wider ends of the tracks would merge to form a liquid bridge. The critical volume at which the liquid bridge occurs depends on the geometrical features of the tracks and their lateral spacing. This provides a design tool for metering precisely the volume of pumped liquid that eventually forms a bridge between the two tracks. The device design we attempt, therefore, comprises of three wedge-shaped tracks; FIG. 5(a). Tracks A and B are 21.5 mm long with wedge angle of 1° spaced parallel to each other at an axis-to-axis pitch of 3.6 mm, while track C, 21.5 mm long with wedge angle of 10° is placed in tandem. A 1.5 mm×0.5 mm rectangular superhydrophilic strip D protrudes from track C between tracks A and B to facilitate the liquid draining process (as described below). Water droplets were dispensed one-at-a-time using metering syringes placed over the narrow ends of tracks A and B and were transported spontaneously to their wider ends, where δ~720 μm. Even with the first pair of droplets (4.7 μL each) deposited, the ratio $\Omega/[\delta(x)]^3$~12.6, which is an order of magnitude higher than the critical value mentioned in [0092]. This is corroborated by the observation of liquid bulges formed at the ends of tracks A and B and their growth until they attain the state shown in FIG. 5(b). For the given spacing between tracks A and B on the aluminum substrate, the two bulges touched at their largest girth (see FIGS. 5(b) and (b1)) after each channel received 7 droplets of 4.7 μL each (i.e., a total of 65.8 μL). FIGS. 5(c) and (c1) show the onset of liquid bridging caused by the merger of the two bulges. The bridge grew immediately due to coalescence of the two volumes (FIGS. 5 (d, e) and (d1, e1)). The liquid bulges had oblong shape (axial extent nearly 2.5 times their lateral spread), as seen from the top in FIG. 5 (b-e); the end view of the same event is shown in FIG. 5 (b1-e1). The bridge height as recorded in FIGS. 5(b1-e1) may be treated as the characteristic bridge dimension during coalescence. Over the first 5 ms of bridge formation, the droplet bridge height grew with the square root of time (see FIG. 15), which is typical of a droplet coalescence scenario where capillary and inertial forces dominate. The liquid bridge eventually touched the intervening superhydrophobic surface (FIG. 5(e1)) and rested on it in a Cassie (non-wetting) state, as is evident from the visible glossy texture underneath it (see white arrow in FIG. 5(e)). The curvature of the liquid bridge is seen to create a "lens" effect so that micro-scale surface texture details of the superhydrophobic region become magnified, and thus more visible. The liquid bridge kept expanding axially due to the inertial effect at the expense of the lateral spread of the bulge when ultimately it touched the narrow end of strip D (see frame 5(g)). The liquid then hemiwicked through the superhydrophilic strip and advanced onto track C when the final stage of pumping began (frame 5(h)). The liquid in the bridge was pumped through track C from t=24 ms through t=208.5 ms (see frames 5(h) through 5(l)) until the pool drained completely and de-bridged from tracks A and B. With continual dispensing of droplets at the loading (narrow) end of tracks A and B, the cycle of bridging, spreading, pumping and de-bridging can be repeated as many times as needed. Between the events of the liquid bridge touching track D (FIG. 5 (g)) and the de-bridging (FIG. 5 (l)), the device pumped at an average rate of 357 μL s$^{-1}$ without any external power input. More importantly, the quantity of transposed volume, which can be controlled by altering the geometry of the tracks, is highly repeatable.

Figure 6:
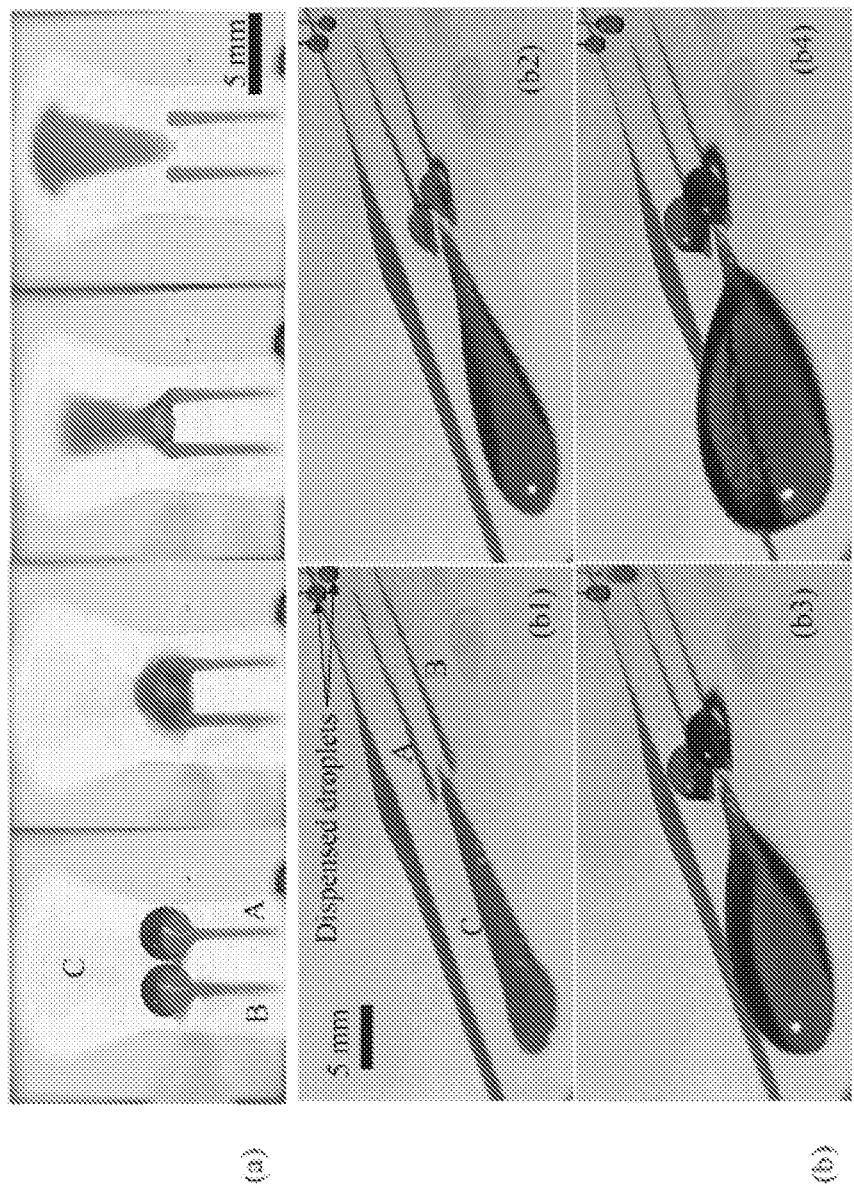
FIG. 6 shows (a) End view sequence displaying liquid bridging and draining on the design of FIG. 5(a) applied on a horizontal paper substrate. (b) Collection of liquid on the bridge circuit on a horizontal transparency (PET) film substrate after pumping for (b1) 1 cycle (~56 $\mu L$), (b2) 4 cycles (~226 $\mu L$), (b3) 7 cycles (~395 $\mu L$), and (b4) 10 cycles (~564 $\mu L$). The liquid (water) is dyed for better visualization.

The design performed equally well on PET film and paper, as it did on metal. FIG. 6(a) shows the different stages of a similar cycle of bridging, pumping and de-bridging on a horizontal paper substrate (the water was dyed red for better visualization). For the same dimensions of track patterns as in FIG. 5 (Al substrate), the bridging of liquid accumulated on tracks A and B in FIG. 6(a) occurred once after each track received 6 droplets (each measuring 4.7 μL), thus pumping approximately 56.4 μL per cycle. Similar pumping behavior was also observed on PET film. FIG. 6(b) shows snapshots of liquid accumulation on a PET film substrate on track C after the device has pumped for 1, 4, 7 and 10 continuous cycles. FIGS. 6(b3) and (b4) show that the drained liquid rests on track C showing a bulge morphology, with the liquid pinned on the wettability contrast line along the periphery of the larger track. The maximum storage capacity of track C is, limited by the track area and the value of $\theta_{Sphobic}$. If the liquid is suitably drained out from the downstream end of track C (e.g., by providing a larger superhydrophilic well or by capillary wicking), the device will pump repeatedly for an indefinite period. On both aluminum and PET film substrates, the design was found to exhibit continual pumping at the same cycle volume until track C is filled up to a level that the contact line could no longer be pinned at the borders of the track. For a paper substrate, the repeatability was compromised by selective imbibition in the substrate itself through the philic track due to prolonged exposure to water. Therefore, for paper based substrates, long-term performance is not warranted. However, the paper-based substrate may be used as an ideal choice for inexpensive single-use microfluidic devices.

Figure 7:
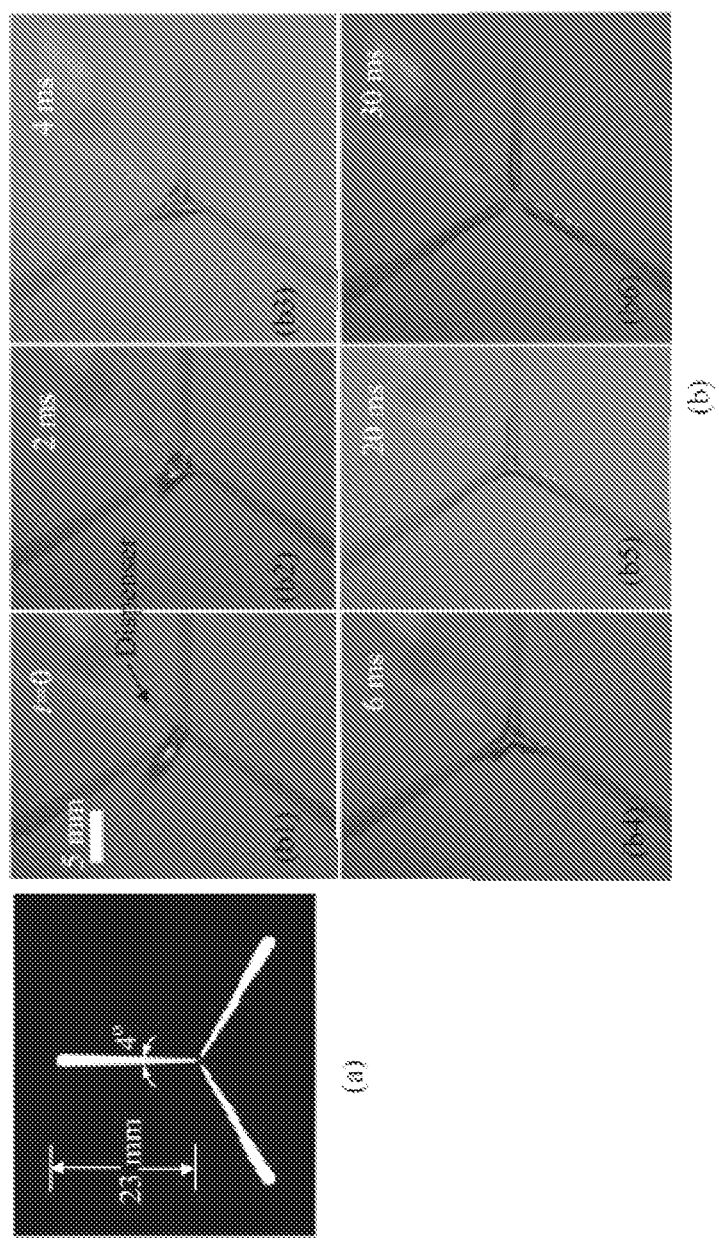
FIG. 7 shows (a) photomasking template for the droplet three-splitter design. (b) Time-lapsed snapshots of a complete cycle of droplet splitting on an Al substrate with 3 laterally equispaced radial wedge tracks. This event achieves a collective average pumping rate of 157 $\mu L\ s^{-1}$.

Droplet splitting in multiple equal volumes. Droplet splitting is an important task in digital microfluidics, as for example when a given sample volume needs to be split for feeding a multiplexed microfluidic architecture. FIG. 7 (a) shows the design of a droplet splitter that has 3 identical wedge-shaped superhydrophilic tracks (23 mm in length, wedge angle 4°), each laid radially outward from a common center at 120° angular spacing. The narrow ends of the wedge-shaped tracks are spaced 800 μm from the center, which is marked by a 400 μm circular hydrophilic spot to allow droplet anchoring during deposition on the substrate. FIGS. 6(b1)-(b6) show the time-lapsed images of an event after a 4.7 μL droplet was deposited on the central philic spot. As the droplet was dispensed on the substrate (FIG. 7(b1)), the outer rim of its base touched the narrow ends of the radial tracks (FIG. 7(b2)) upon impact; the liquid quickly spread along the superhydrophilic radial tracks, forming a liquid bridge that connected the three tracks and the central philic spot (FIG. 7(b3)). The pumping continued from the central spot with a liquid front propagating along each track (FIG. 7(b4, b5)) till the central liquid volume de-bridged at the inner ends of the track (FIG. 7(b6)), leaving a very small residual droplet at the central philic spot. The salient advantage of this design is that the residual central volume is much smaller than the original droplet volume, with no liquid bridging the split radial volumes. Thus, for an LOC application this design eliminates the possibility of cross-contamination. As observed from the timestamps in FIG. 7(b), the droplet took 30 ms to fragment between the central spot and the three radial tracks corresponding to a pumping rate of ~157 μL s$^{-1}$. For a uniform split, each track in FIG. 7 transported ~1.5 μL volume. The splitter design was also successfully tested on paper and PET film. It is important to note that irrespectively of the substrate, the uniformity of volumes collected at the end of each track is found to be very sensitive to the precision with which the original droplet is deposited on the central spot. Any eccentricity or bias in the position of the liquid dispenser leads to unequal liquid distribution. This feature can therefore be used as a tool for two-dimensional microfluidic position sensing. Splitter designs with higher number of radial arms (with same track size and distance of inner ends from central philic spot) are also demonstrated in FIG. 16c where each splitter arm is shown to transport ~1 μL liquid per cycle.

Figure 8:
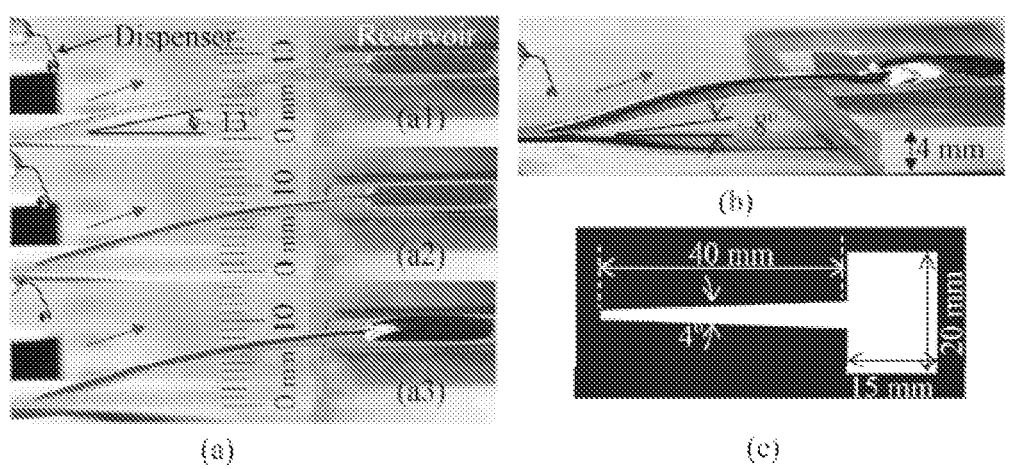
FIG. 8 shows transport of liquid up along an inclined superhydrophilic wedge-shaped track. (a) Snapshots of water droplets (dyed for better visualization) being pumped up along a transparency (PET) film substrate to an elevation of 9 mm after: (a1) one drop (4.7 $\mu L$), (a2) 5 drops (23.5 $\mu L$), and (a3) 40 drops (188 $\mu L$). (b) 25 droplets (117.5 $\mu L$) were pumped up a height of 4 mm along an identical track on paper. (c) The photomasking template for the tracks used in (a) and (b).

Liquid transport up an incline. Use of flexible substrates like paper and transparency (PET) films allows the ability to attain out-of-plane liquid transport. In order to realize such transport, the capillary force has to overcome gravity in part of the microfluidic circuit. The wedge-shaped superhydrophilic tracks on a superhydrophobic paper or PET film surface have already been found capable of producing rapid liquid transport on horizontal substrates. FIG. 8 shows that the capillary force produced on the droplet by the wedge-shaped track is also strong enough to move the liquid up along an inclined substrate. FIG. 8(a1-a3) shows images of liquid being pumped up a ramp to an elevation of 9 mm. This corresponds to an approximate ramp tilt angle of 13° for the flexible PET film substrate, although the ramp appears slightly curved due to the flexibility of the PET film. FIGS. 8(a2 and a3) show a residual volume of liquid left behind on the inclined superhydrophilic track after pumping a given volume to the reservoir on the top. After transporting a total of 50 drops (235 μL) of water up the ramp, the track was found to retain only 14 μL, a small portion of the total volume propelled to the top. Similar pumping was also observed on paper where the same design was found to transport 117.5 μL of water up a height of 4 mm along a ramp angle of ~8°; see FIG. 8(b). FIG. 8(c) depicts the template design used for the PET and paper substrates.

Figure 9:
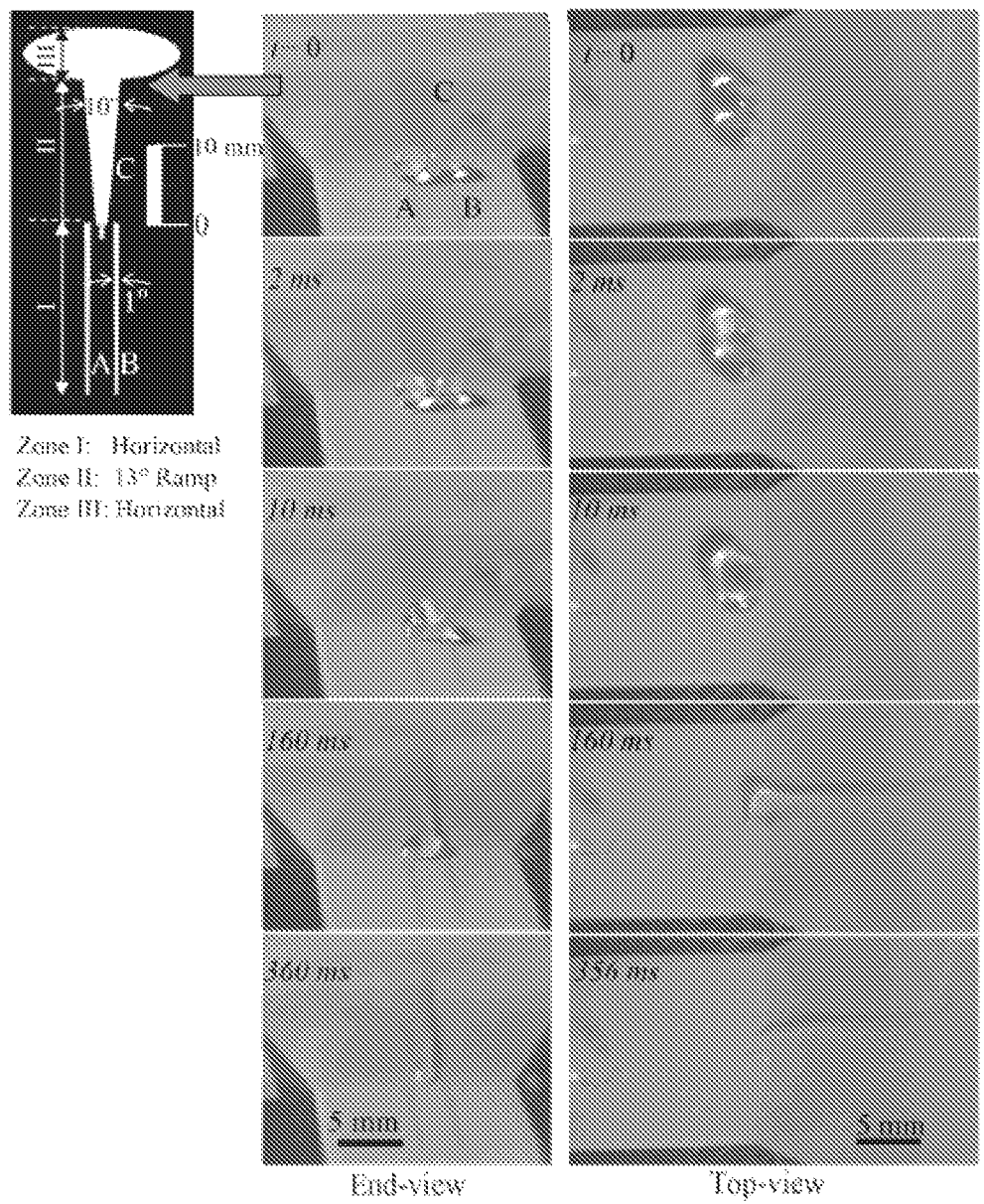
FIG. 9 shows snapshots of liquid transport up an inclined plane through a 13' up slope (height of ~4 mm) on a droplet bridging and draining circuit (inset at the top left corner) after dispensing 56.4 $\mu L$ of liquid (one droplet at a time). End-view (left column) and top view (right column), as taken from two distinct runs under the same conditions. The needle dispenser can be seen on the left of each top-view image.

Pumping of liquid against gravity by the wedge-shaped superhydrophilic pattern works well also for the liquid bridging/draining circuit (FIGS. 5, 6). A PET substrate was used to create a three-dimensional platform where the substrate had two horizontal parts at two different elevations, connected by an inclined section. FIG. 9 shows select snapshots as a liquid bridge formed between two parallel wedge-shaped tracks A and B on the horizontal part (I) of the substrate, and then the bridged liquid was pumped along the third track C (II), laid on the inclined part of the substrate at 13° tilt up to a height of 4 mm. The bridging, draining and de-bridging modes of liquid transport on the non-planar substrate were similar to those observed on a horizontal surface (FIGS. 5 and 6), with the only difference that the pumping rate for the inclined substrate was ~156 μL s$^{-1}$ as opposed to 357 μL s$^{-1}$ on the horizontal plane. All the cases presented in FIGS. 8 and 9 showed pumpless transport, where the spatial difference of surface energy on the substrate is utilized to overcome the viscous resistance and gravity force. In principle, the technique works with a combination of up and down ramps, thus offering limitless possibilities for the construction of 3-D microfluidic arrangements that are capable of transporting liquid at considerable rates. The present examples demonstrate the prospect of complicated microfluidic networks (e.g., open channels in the form of crossovers) on microfluidic platforms for enhanced device functionality.

Example 4

Surface Wettability Characterization

Contact angle measurements were performed on the bare and coated (superhydrophobic and superhydrophilic parts)

aluminum, paper and PET substrates. Both aluminum and paper exhibited sessile contact angles slightly less than 90°. The PET substrate showed strong wettability (apparently due to a commercial coating on the transparency film used in the experiment). See FIG. 10.

Example 5

Variation of Capillary Force on Droplet with Wedge Angle α and Liquid Volume Ω

Figure 11:
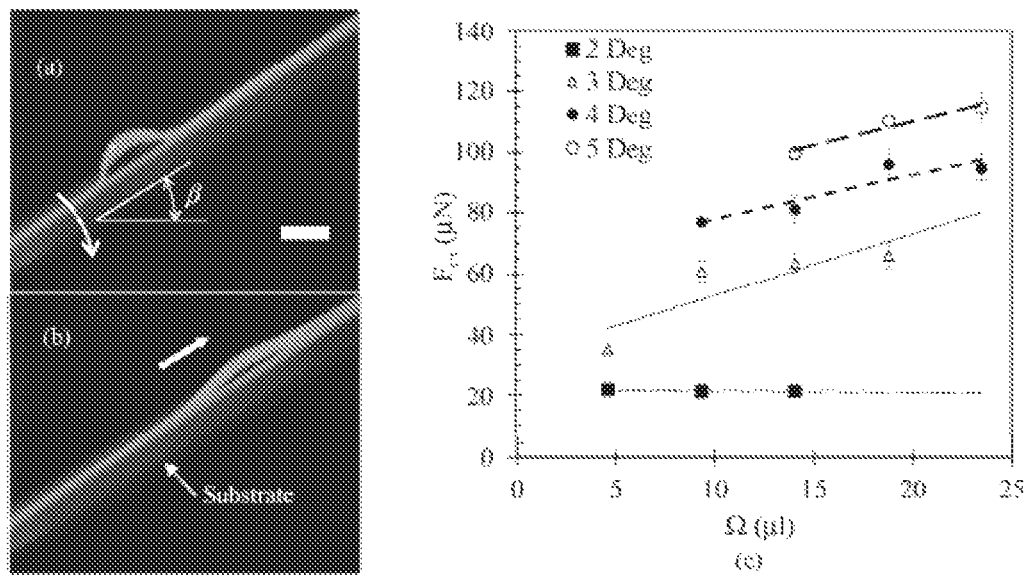
FIG. 11 shows an image of the liquid accumulation on the inclined wedge-track (a) just before the inclination angle β reached the critical value below which the liquid bulge started moving up the plane, as shown in (b). (c) Variation of the capillary force on the droplet with droplet volume Ω for different values of wedge angle α. Scale bar denotes 2 mm.

To confirm the validity of Eq. (2), which indicates that the Laplace pressure gradient on a droplet placed on the wedge-shaped track is proportional to the wedge angle—as long as a is small—we carried out a separate experiment (see FIG. 3($a$)) for evaluating the capillary force on the droplet as it began its journey from the narrow end on the track. The experiment was repeated for wedge angles of 0, 2, 3, 4 and 5 degrees. The superhydrophilic tracks were presuffused with water and droplets of known volumes were deposited. The substrates were initially tilted with the wider end up at an angle steep enough so that the forward (i.e., up-slope) capillary force on the liquid bulge could not overcome its in-plane component of weight (acting down-slope), thus keeping the droplet pinned at the narrower end of the track (FIG. 11($a$)). Inclination (β) of the substrate was very slowly decreased until the inplane component of the droplet weight became lower than the capillary force and the droplet started moving up the plane (FIG. 11($b$)). For rectangular tracks (a=0°) the liquid bulge deposited on the track did not move (although capillary spreading of the liquid front was observed) even for β=0 (horizontal surface). For higher wedge angles, the inclination β marking the impending motion of droplets was also higher, implying that the capillary force increased with α. The capillary force on the liquid bulge, as Eq. (2) suggests, also depends on $\theta_{avg}$, which should be a function of the dispensed droplet volume Ω. In order to explore this dependence, we deposited droplets ranging from 4.7-23.5 μl and recorded the corresponding values of b. FIG. 11($c$) shows the variation of capillary force $F_{cx}$ with droplet volume Ω for different wedge angles. Each data point was obtained from averaging 60 to 300 readings, while the error bars denote the standard deviation in these readings. For larger wedge angles (α=4° and 5°) the capillary force was too strong to be countered by the weight of small volume droplets, and hence only larger volumes of droplet had to be dispensed. For all the substrates, the droplet volume was found not to influence the capillary force strongly. Therefore, the average $F_{cx}$ values of FIG. 3($b$) were plotted using the data sets for each value of α in FIG. 11($c$) by averaging over the entire range of droplet volumes used for each α.

Example 6

Holding Capacity of a Wedge Structure

For an isolated superhydrophilic wedge-track of finite length on a superhydrophobic background, liquid that is transported from the narrow to the wide end remains confined in the track. If the track is wide enough, the liquid builds up initially creating a rising rivulet from the narrow to the wide end. Further addition of liquid shows that the track retains its pumping ability, with the accumulating height increasing further. When $\Omega/\delta^3$ exceeds a critical value, a liquid bulge becomes wider that the wide end of the track. For a track of 60 mm length and 4° wedge angle the wider end measures δ ~4.2 mm; the bulge at the wide end did not evolve until 50 droplets of 4.7 μL each were deposited at the narrow end and transported there, leading to $\Omega/\delta^3=(235/4.2^3)=3.17$ (see FIG. 12).

Example 7

Effect of Pre-Wetting (Presuffusing) the Track

Supplementary movie SM1 shows the transport of water droplet on a 4o wedge track; the movie is played at ⅓₀th of its real-time speed. In the movie, the droplet was intentionally pinned to the dispensing needle for about two seconds (when its lower end touched the track) to allow a presuffusing front to proceed visibly ahead of the liquid pool (see the ~3.5 mm dark presuffused track in the movie at its opening frame). FIG. 13 shows the effect of presuffusing on the capillary pore diameter that is driving hemiwicking. For a dry track, hemiwicking speed is limited by the smallest (deepest) roughness features on the surface. On a presuffused track, these smallest features are already submerged in liquid, leaving larger length-scale features, which in turn limit the hemiwicking speed. Since the latter scales linearly with pore diameter, liquid velocity is higher on the presuffused track.

Example 8

Effect of Droplet Acceleration at t=0

Figure 14:
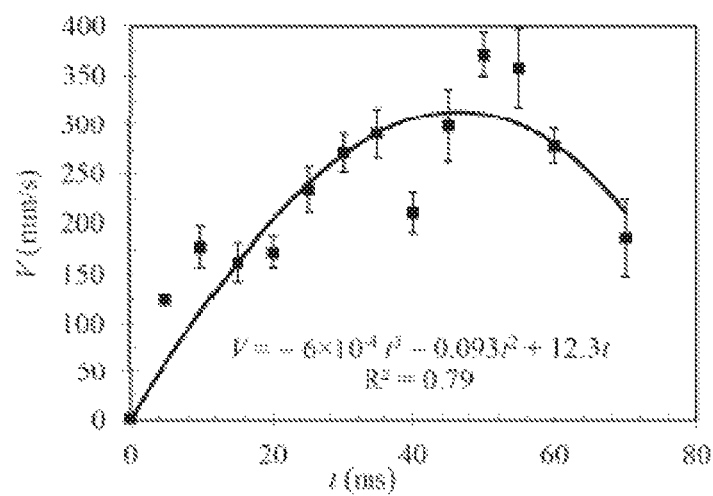
FIG. 14 shows velocity-time plot of the liquid bulge on a horizontal presuffused track with α=3°.

FIG. 14 shows the velocity of the liquid bulge as a function of time as it moved along the presuffused track with α=3°; see FIG. 4($a$) for the corresponding x vs. t plot. As discussed in the main text, the liquid bulge starts from rest due to its inertia. A cubic polynomial best fit indicates that the acceleration of the liquid bulge at the inception of the droplet motion was $dV/dt|_{t=0}=12.3$ m/s². This matches closely with the acceleration (12 m/s²) measured for a 4.7 μL droplet that was driven by a capillary force of 56.3 μN (see FIG. 3($b$)) on a tilted surface.

Example 9

Capillary Bridging

Capillary bridging of the liquid bulges at the wider ends of tracks A and B took place where the surfaces of the two bulges touched. The bridge formed in the air (i.e., the liquid bridge does not touch the substrate at t=0) with an initial thickness $h_0$. The two adjacent bulges, which remained pinned to the superhydrophilic tracks, coalesced through progressive growth of the liquid bridge. The width h of the capillary bridge (as seen from the end view reported in FIG. 5($b$1)-($e$1)) is plotted in FIG. 15 for four different runs. The growth rate $h/h_0$ was found to scale with $t^{1/2}$, which is typical of inertia-driven coalescence (for viscous-driven flow the dependence would have been proportional to t).

Example 10

Droplet Splitting on Paper and PET Films

Figure 16:
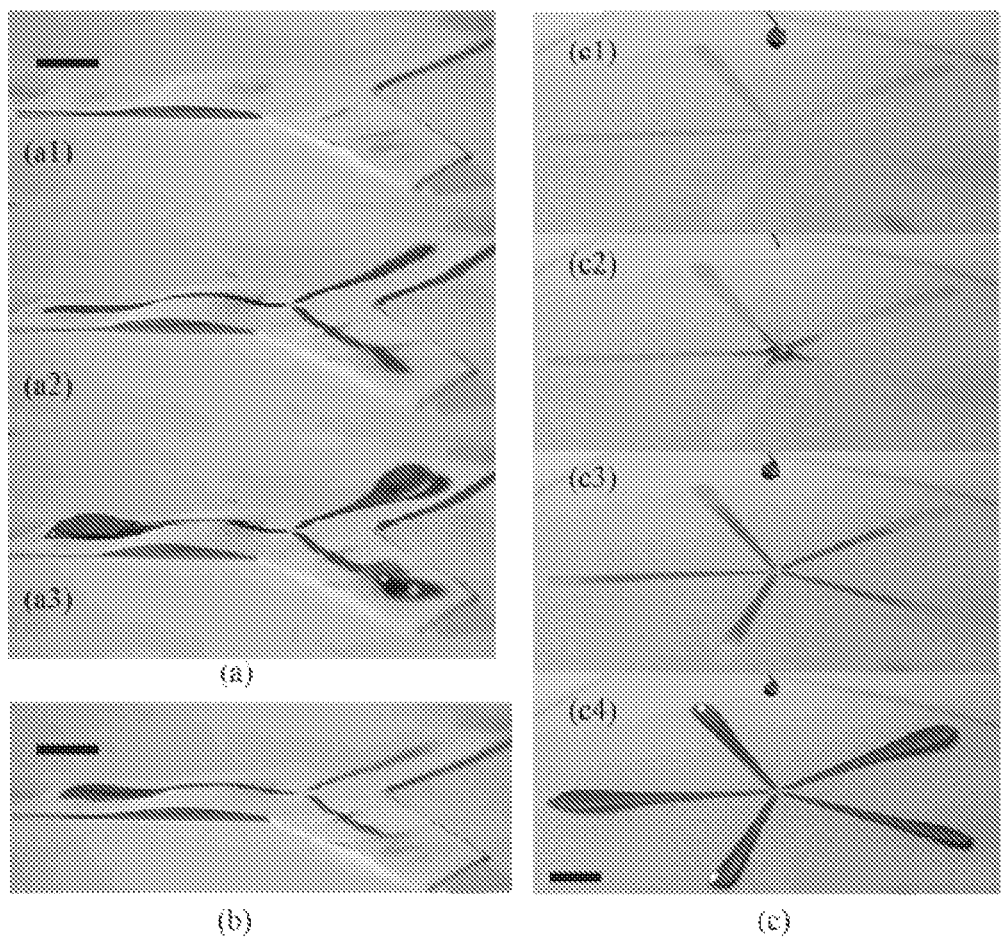
FIG. 16 shows (a-b) Droplet three-way radial splitting on a paper substrate. (a1) The substrate, (a2) liquid accumulation after perfectly symmetric deposition of 5 drops (23.5 $\mu L$) at the center, (a3) same, after 15 drops (70.5 $\mu L$). (b) Biased accumulation after asymmetric splitting of 5 successively dispensed droplets. (c) Droplet 5-way splitting on transparency (PET) film: (c1-c3): sequence of the first droplet split, (c4) liquid accumulation after splitting of 10 droplets (47 $\mu L$). Scale bars denote 5 mm.

Like the droplet bridging circuit, the droplet splitter design also worked equally well on paper and PET substrates. FIG. 16($a$) shows the images of the three-track design on paper, while FIGS. 16($b$) and ($c$) show the images of the split volumes of water (colored for visualization) after dispensing 5 (23.5 µL) and 15 droplets (70.5 µL), respectively. To demonstrate how any eccentricity or bias in the position of the liquid dispenser leads to unequal degrees of liquid distribution along the splitter limbs, we dispensed 5 droplets (23.5 µL) with an offset of ~100 µm from the center spot. FIG. 16(*b*) shows the extent of the resulting unequal liquid distribution. FIG. 16(*c*1-*c*4) shows droplet splitting in a 5-splitter design on PET film. The bridged droplet at the early stage of splitting can be seen in frame (c2), while frame (c3) shows the nearly even distribution of the liquid after the split is complete. The central spot can be seen to retain a very small volume. The splitting continues for several consecutive droplets released until the accumulated liquid volume in the radial tracks eventually deters the de-bridging of the central droplet at the end of pumping. FIG. 16(*c*4) shows the liquid accumulation at the end of splitting of 10 consecutive droplets (47 µL). This particular design on PET film has been found to work with repeatable features up to 17 consecutive splitting droplets (~80 µL).

Example 11

Curved Track Designs

The track designs should not necessarily be restricted by straight boundaries; the boundaries between wettable and non-wettable domains may be curved. For example, FIG. 17(*a*)-(*d*) shows snapshots of three-dimensional liquid transport on a combination of a straight (horizontal) and a curved (ramp) wedge track designs laid on flexible PET films, which are arranged in an "highway overpass" design. FIG. 17(*a*) shows two tracks before dispensing the liquid droplets, while (b) and (c) show images at 0.5 and 3.0 s after dispensing the first droplet pair (green and blue, 4.7 µL each); (d) shows the same after 17 identical droplets (~80 µL of liquid) have been transported on the curved (ramp) track and 28 droplets (130 µL) on the straight one. The corresponding design template of the photomask is shown in FIG. 17(*e*). The curved track is observed to pump the red-dyed liquid to the reservoir on the left side, passing over the highest peak (~5 mm above the horizontal substrate). This three-dimensional transport feature offers the possibility of laying interwoven complex circuits of open microfluidic channels passing over others without cross-contamination of liquids. FIG. 17(*f*) shows liquid (red) transport on a gradually widening spiral superhydrophilic track (inset shows the template design of the photomask).

Example 12

Materials and Methods for Examples 13 to 16

Materials: The chemicals used comprise a fluoroalkylsilane, abbreviated as FAS (1-H, 1-H, 2H, 2H-Perfluorodecyl triethoxysilane, Sigma Aldrich), hydrochloric acid (Sigma Aldrich, 36% in aqueous solution) and ethanol (~100 wt. %, Decon Labs). The substrate was a mirror-finish aluminum plate (multipurpose polished aluminum alloy 6061, 2 mm thick, McMaster Carr) coated with a protective polymer sheet, which can be ablated in $CO_2$ laser cutting. The FAS chemical served as the primary component attributing to the superhydrophobicity of the superbiphilic substrates. Etching by HCl imparted the required micro- and nanoscale roughness and promoted superhydrophilicity. All of the above materials were obtained off-the-shelf and are readily available in the market.

Figure 18:
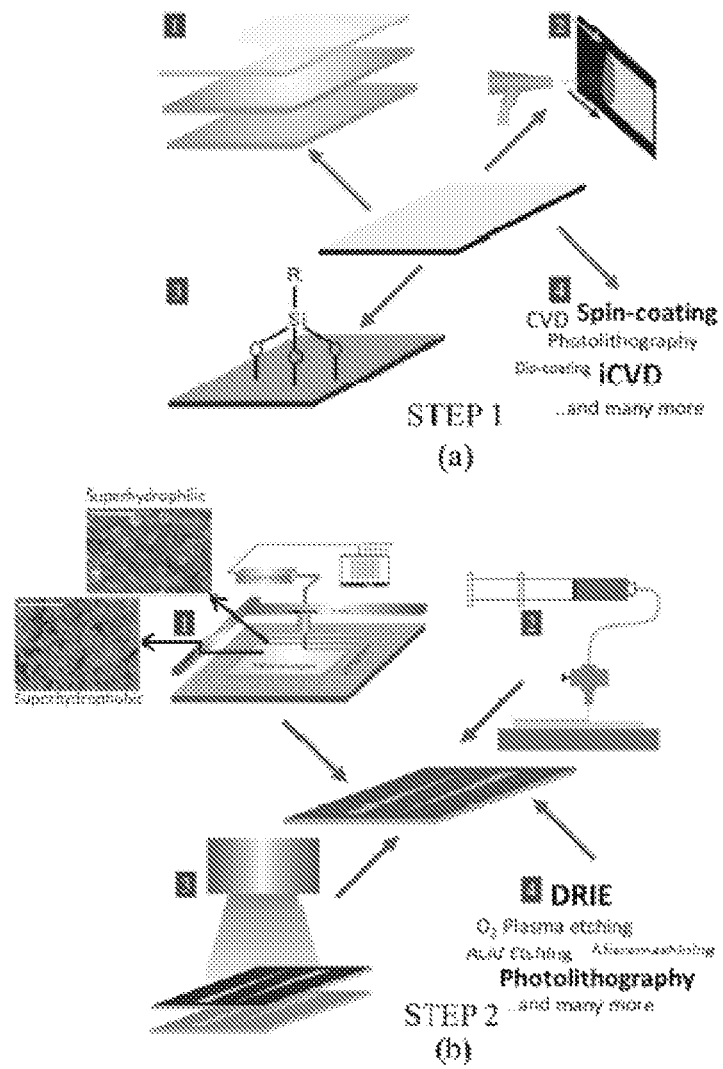
FIG. 18 shows different ways of making (a) superhydrophobic surface and (b) wettability patterned surfaces. In Step 1, substrates (1) are made superhydrophobic/phobic by spraying (2), adding fluoroalkylsilane monolayers (3) or other available methods (4). In Step 2, patterning of superhydrophilic designs are done by laser ablation (inset: SEM images of laser-ablated superhydrophilic and fluoroalkylsilane monolayers coated superhydrophobic surfaces; scale bar 100 $\mu m$) (1), printing superhydrophilic ink of a complimentary background (2), UV exposure to selected photo masked regions (3) as well as numerous other available methods (4) to create a wettability contrast substrate.
Figure 27:
FIG. 27 shows sessile water droplets on mirror-finish hydrophilic aluminum (left), and micro-nanostructured superhydrophobic aluminum (right). The Table shows the contact angles for the different regions of the Type I and Type II substrates.

Sample preparation: We used a facile and scalable approach to fabricate samples with alternate regions of contrast wettability as per the pattern designs. Keeping in mind both the mild and high vapor content environments in typical condensing scenarios (i.e., low and high heat flux conditions), we chose to study two types of material systems for wettability patterned substrates—the first one (Type I) comprising of superhydrophobic-superhydrophilic domains, while the second one (Type II) had hydrophilic-superhydrophilic domains. Type I substrates were prepared by creating superhydrophobic background on the substrate followed by laser etching to create superhydrophilic tracks. Custom sized (127 mm×85 mm) aluminum plates were dipped in 3M HCl acid bath for 15 minutes to etch and create micro-nano roughness features. The etched substrates were then immersed in boiling water for 1 hour which rendered the surfaces superhydrophilic. Next, the substrates were air-dried and then immersed in solution of 1% FAS in ethanol for 1 hour. Subsequently, the substrates were dried in an oven at 80° C. for 30 minutes to evaporate any residual ethanol. The above steps rendered the substrates superhydrophobic. Suitable CAD designs of the patterns were fed to the computer of a $CO_2$ laser (Universal Laser Systems, VLS 6.60, 10-60 W) in a raster mode and selected regions of the superhydrophobic substrate were laser-ablated at optimized power and speed (80% power and 4% speed) settings of the laser-head. The laser ablated regions turned superhydrophilic (see the SEM image in FIG. 18(*b*1)). The resulting substrate exhibited patterned wettability with sessile contact angles θ~153.7°±2.0 for the superhydrophobic and 0° for the superhydrophilic region (see Table in FIG. 27).

For Type II substrates, we used the intrinsic wettability of mirror finish aluminum for the philic region ($θ_e$~78.2°±2.0, see Table in FIG. 27) and apply spatially selective chemical etching to create the superhydrophilic tracks on it. This method consumed less chemicals than the Type I and avoided use of any fluorinated chemical. A CAD file of the pattern design was fed into the computer-controlled $CO_2$ laser, as a vector image; the laser cut (at 5% power and 6.7% speed settings) through the polymer cover sheet on top of the substrate (FIG. 18(*b*)). The polymer sheet was selectively peeled from the areas to be exposed to acid treatment and water boiling (similar to that followed for the Type I substrate). The final outcome of the entire process was a wettability patterned substrate with alternate superhydrophilic and superhydrophilic domains.

Characterization: Surface characterization was done through measurements of contact angle, scanning electron micrograph (SEM) of regions of interest on the sample. We used a custom built goniometer using a CCD camera (Pulnix, Model TM-9701) mounted with an OPTEM ZOOM 100 lens. The droplets were backlit by a cold light source (FOSTEC, 8375). Standard image analysis software (IMAGE-J) was used to calculate the contact angle, advancing, receding angles and the roll off angles (see FIG. 27).

Figure 19:
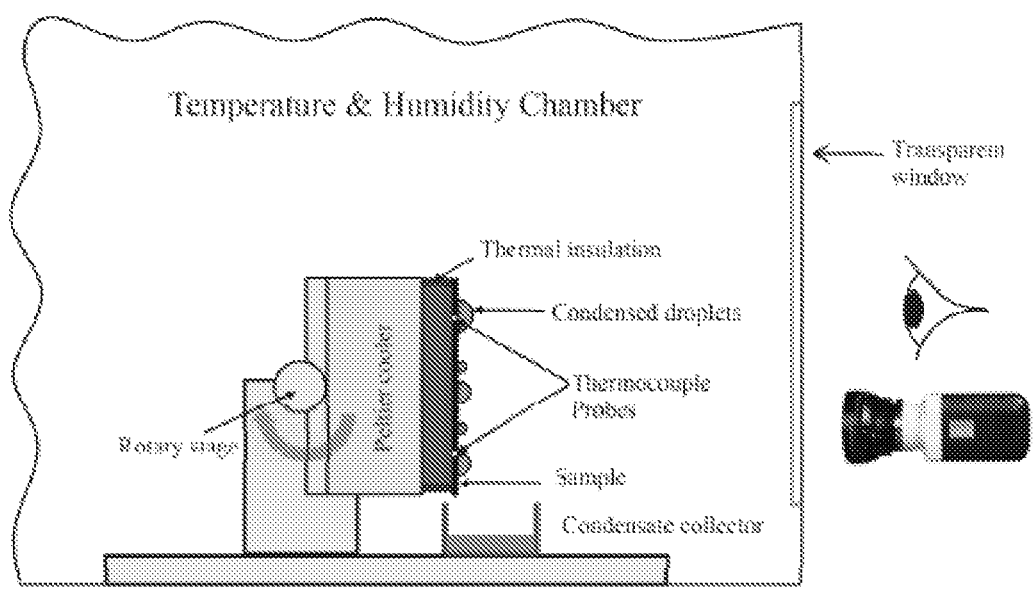
FIG. 19 shows a condensation experiment setup. Testing samples were mounted on computer controlled Peltier cooler which further controls the substrate surface temperature. The entire Peltier mounted stage was kept in a humidity and temperature controlled environmental chamber. Visualization was done through a heated (to prevent fogging) glass window using high-speed photography.

Experiments and Image Analysis: The condensation experiments were conducted in a temperature- and humidity-controlled environmental chamber (ESPEQ, SH-641), with experiments conducted at various dry bulb temperature (DBT) and relative humidity (RH) settings. FIG. 19 shows a schematic of the experimental setup. The sample was mounted vertically using a thermally conductive adhesive tape (Mc Master Carr, 6838A11) on the cold plate of a Peltier cooler (TeTech, CP-061). The sub-cooling of the sample surface was maintained by controlling the Peltier cooler at a set temperature of 0° C. The temperature readings of the sample surface (which was at slightly higher than the Peltier set temperature due to the thermal resistance of the Peltier base plate and the contact resistance between the sample and Peltier plates) were monitored by mounting four K-type thermocouples (Omega) to the sample plate; thermocouple probes were inserted in 800 μm holes drilled beneath the condensing surface of the sample plate where they were mounted with thermally conductive silver paste, Omegatherm™ 201, Omega) and recorded in real time using a DAQ (Omega, USB 2400 series) at 1 Hz sampling frequency. Experiments were repeated at similar conditions for the control case (mirror-finish, hydrophilic bare aluminum), Type I and Type II surfaces and their condensation rates were compared. Condensate collected over a specified duration were weighed in a commercial digital balance (least count 0.01 gm). Sub-millimeter scale and millisecond duration events of condensation dynamics were imaged at 2000 fps using a high-speed CCD camera (Phantom Miro 310) with an OPTEM ZOOM 100 lens; suitable illumination was achieved by a light source (FOSTEC, 8375). The real-time condensate droplet distribution were recorded using a standard DSLR (C 70-300 mm). Captured images were processed using MATLAB image analysis tool.

Example 13

Control of Droplet Growth and Condensate Drainage

Figure 20:
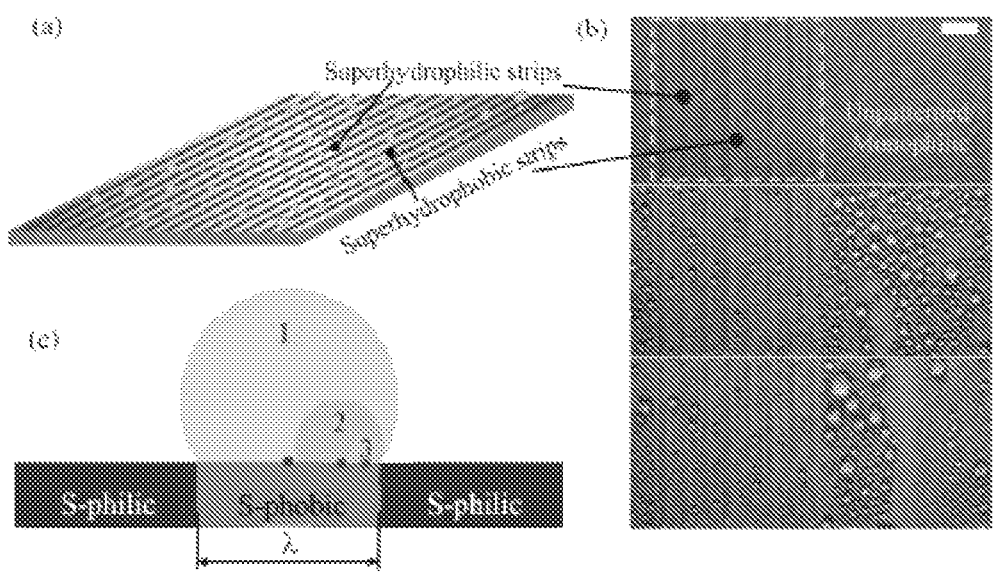
FIG. 20 shows (a) schematic of the biphilic (superhydrophilic-superhydrophobic) pattern used in (b) Type-I surface: Equally spaced 1250 $\mu m$ wide superhydrophobic parallel stripes separated by 400 $\mu m$ superhydrophilic tracks showing droplet size control in condensing environmental over time. Each of the images is taken 15 minutes apart. Unpatterned region (right half) exhibits a much greater droplet size compared to patterned region (left half). Scale bar (white) is 3 mm. (c) The largest condensate droplet (shown in different colors) size depends on location of point of nucleation (the dark dots) on the S-phobic region. The closer the point of nucleation to the wettability contrast line, the smaller the size of the departing droplet (drawn into the superhydrophilic strip).

By providing wettability-patterned substrates comprising juxtaposed regions of high and low wettability, a sustained mechanism for control of droplet growth and condensate drainage can be achieved. While the less wettable area of the surface offers the sites for droplet nucleation and growth in a dropwise manner, the more wettable regions (occupying a smaller fraction of the total area) offers the path for condensate drainage (FIG. 20($a$)). To test our hypothesis, we first compare DWC on homogeneous superhydrophobic (monophilic) surface with that on a Type I (superhydrophobic-superhydrophilic) wettability-patterned surface in the environment chamber at an ambient condition of 20° C. DBT and 80% RH (the Peltier plate was held at 0° C.). To eliminate variability associated with substrate temperature, the monophilic and wettability-patterned surfaces were laid side by side on the same plate. On the Type I pattern, the width of the superhydrophobic regions was 1250 μm (nearly half of the capillary length for water, which is 2700 μm) while the width of the superhydrophilic track was 400 μm. As the plate temperature fell below the dew point temperature (16.5° C. in this case) condensate droplets started to appear on the superhydrophobic parts of the plate; no droplet was seen on the superhydrophilic tracks as the condensate spread quickly along the track length due to hemiwicking. With passage of time the droplets on the superhydrophobic surface grew; neighboring droplets merged as they touched. Merged droplets were found to grow further, exhibit occasional out-of-plane jumping, or be shed by gravity if they grew beyond a threshold size. Area under the displaced or removed droplet opened up surface for fresh nucleation and growth of condensate (droplet rejuvenation). All these features were in common with the standard observation of DWC on superhydrophobic surfaces. However, the unique feature was that the maximum droplet size appearing on the superhydrophobic segments of the wettability-patterned Type I region were smaller than their counterparts in the monophilic-superhydrophobic regions. FIG. 20($b$) shows the time evolution of the condensate droplets on the superhydrophobic-monophilic and the wettability-patterned Type I regions at t=0 (b1) and after 15 (b2) and 30 (b3) minutes. Droplets in the patterned region appears visibly smaller than those in the unpatterned monophilic region in FIGS. 20($b$2) and ($b$3). Also the droplet rejuvenation was found to be more frequent in the patterned region than in the monophilic areas.

The largest size $D_{max}$ of a droplet that can be dislodged from an inclined (at an angle of tilt β) condenser surface by gravity depends on the droplet liquid surface tension σ, contact angle θ, and the contact angle hysteresis (the difference between the advancing and receding angles, $θ_a$ and $θ_r$, respectively) so that $$D_{max}=2[3σ(\cos θ_r-\cos θ_a)\sin θ/ρg \sin β(2-3 \cos θ+\cos^3 θ)]^{1/2} \quad (4)$$

Considering $θ_a$=167.4°, $θ_r$=153.7° and θ=163.8° for the superhydrophobic surface (see FIG. 27), β=90° (vertical plate), σ=72 mN m$^{-1}$, the theoretical upper limit of droplet size on the monophilic region of the plate in FIG. 20($b$) should be $D_{max}$~1320 μm, which is close to the observed maximum droplet size (see FIG. 20($b$3)).

Figure 21:
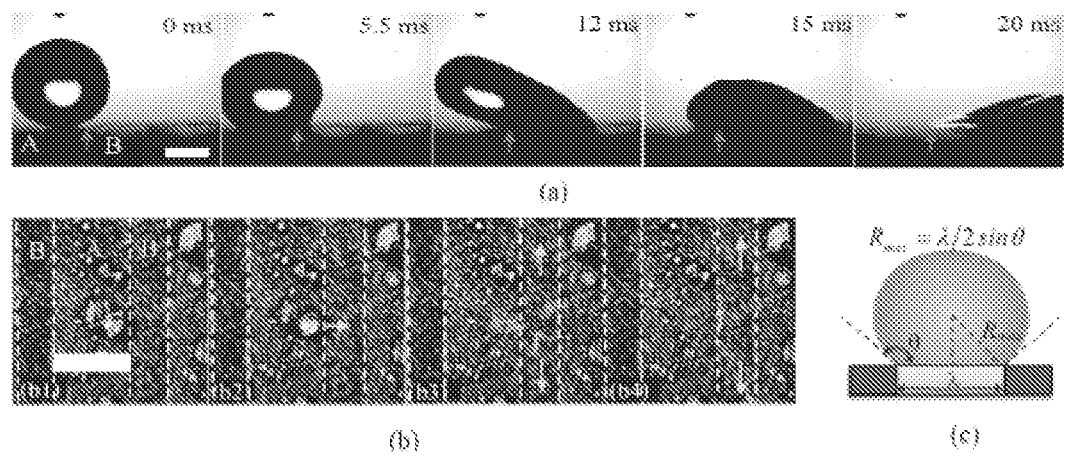
FIG. 21 shows (a) typical dynamics of capillary-driven motion of a drop across the wettability transition line (shown by red arrow) that separates the superhydrophobic A and superhydrophilic B regions. The same mechanism affects condensate removal by capillary pumping along the superhydrophilic track. (b) Droplet growing on the superhydrophobic region (A) adjacent to a superhydrophilic track (B) would eventually touch the track (b1, b2). Capillary pressure in the droplet pumps the liquid into the adjacent superhydrophilic track (b3). Images in (b) are taken every 500 μs apart. The white scale bar denotes 1000 μm both for (a) and (b). (c) Relation between the theoretical maximum droplet diameter and the width 2, of the superhydrophilic track.

In the wettability-patterned region the droplet departure is expected to take place primarily due to their premature draining into the superhydrophilic tracks. The schematic in FIG. 20($c$) shows that the departing droplet size is largely dependent on the location of its nucleation site on the superhydrophobic strip of width λ interspaced between the superhydrophilic tracks. An isolated droplet nucleated from the center of the superhydrophobic region is likely to grow until its rim touches the superhydrophilic strip at both ends; the liquid is then pumped into the superhydrophilic strip due to the capillary pressure of the droplet. Clearly, a droplet nucleated closer to the wettability transition line (demarcating the superhydrophilic and superhydrophilic) would be swept to the superhydrophilic region at a smaller radius. For example, droplet 1 (the dark dot denoting the nucleation site), which has originated more towards the center of the strip would touch the superhydrophilic strips at a larger drop radius as compared to droplets 2 and 3, which are closer to the wettability transition line. The superhydrophilic region becomes wetted with a film of liquid due to occurrence of FWC; further condensation of liquid on the film takes place at a much lower rate since homogenous nucleation rate is very small as compared to heterogeneous nucleation rate on solid surface. As soon as the droplet touches the superhydrophilic region, the capillary pressure difference between the liquid in the droplet and the superhydrophilic track (due to the difference in curvature) leads to rapid pumping of the droplet. FIG. 21($a$) shows such a rapid transition of a sessile water droplet across the wettability contrast line; the 4.7 μL droplet is found to transit across the wettability transition in about 15 milliseconds, corresponding to a volume flow rate ~330 μl/s. For a transition flow taking place across a wettability transition line of ~2 mm length, this represents a very high flow rate. In a condensing scenario, such rapid transport offers an effective mechanism of surface rejuvenation and condensate drainage—see FIGS. 21($b$1-$b$4), where a condensate droplet is seen touching the superhydrophilic line and then being pumped due capillary pressure difference. Theoretically, this mode of capillary pumping in a striped biphilic patterned surface would produce a maximum possible droplet diameter of $D_{max}$=4480 μm. However, careful observation of FIGS. 20($b$) and 21($b$) reveals that the maximum droplet radius was much smaller than that, implying that other mechanisms of droplet removal was also pervasive.

Figure 22:
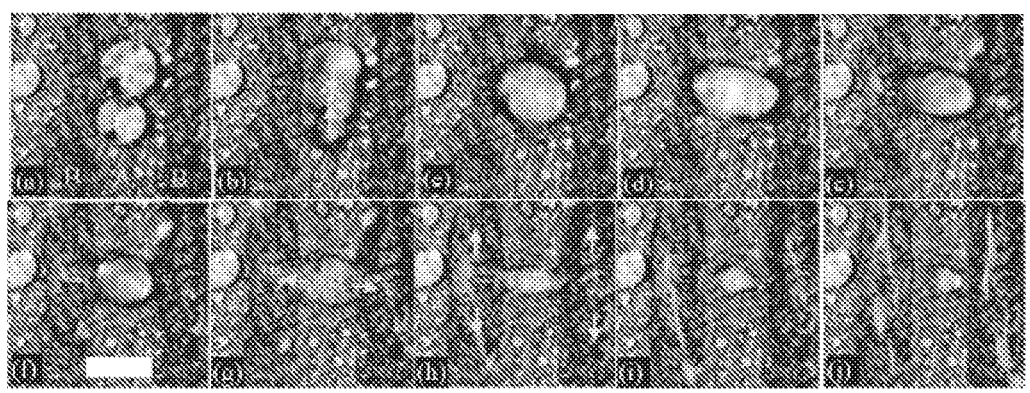
FIG. 22 shows condensate removal followed by droplet coalescence. Two isolated neighboring droplets (a) grow on the superhydrophobic region (A) to touch at their periphery and coalesce (b); inertia of the liquid in the coalescing droplets lead to lateral widening of the bulge (c and d), which touches the two adjacent superhydrophilic (B) tracks. The liquid is pumped into the superhydrophilic track due to capillary pressure within the coalesced droplet (e-j). The white scale bar denotes 1 mm. Images are taken every 500 μs apart.

High-speed imaging of the condensing surface also enabled us to observe and identify another droplet removal mechanism than that hypothesized in FIG. 21. Random droplet coalescence often led to droplet deformation, leading to their spillover on the superhydrophilic track and subsequent pumping. For example, two individual drops of size≈O (100 μm) growing nearly from the central region of the superhydrophilic strip are seen coalescing (FIG. 22(*a-c*)). Momentum of the droplet resulting from the surface energy minimization during coalescence led to transverse bulging of the coalesced droplet (FIG. 22(*d*)); the bulged section of the droplet touched the superhydrophilic region on both sides and was drained subsequently (FIG. 22(*e-j*)). In this case the droplets were removed much before they could grow to $D_{max}=\lambda/\sin\theta$. As mentioned before, condensate droplets on superhydrophobic surface also exhibited out-of plane jumping upon coalescence, which led to further reduction in the maximum droplet size.

Figure 23:
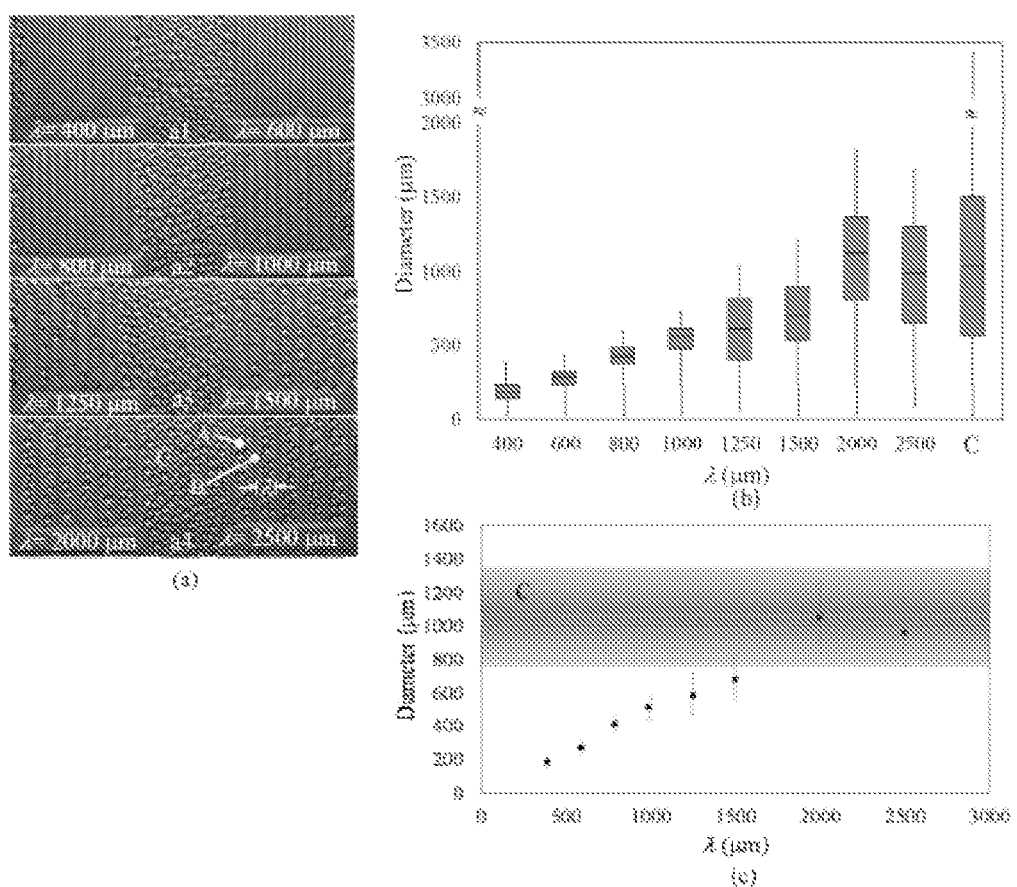
FIG. 23 shows (a) droplet size distribution on biphilic condensing surfaces comprising of less wettable (Type II) strips (A) of width λ interspaced by the superhydrophilic (chemically etched) tracks (B). Region C denotes unpatterned/monophilic bare Al region. (b) Variation of the maximum droplet diameter (averaged over the less wettable strips during a steady condensation period of 30 minutes) with λ. The box plot presents the median, lower and upper quartiles (25th and 75th percentiles, respectively) size of the largest departing droplet recorded at 1 minute interval over the duration of experiment. (c) Variation of the maximum droplet departure diameter ($D_{max}$, averaged over a time period of 30 minutes of steady condensation) with λ. The middle white line in the gray band is the average $D_{max}$ of unpatterned/monophilic region (the gray band denotes standard deviation). Each data point is averaged from more than 300 readings.

Having established the ability of the striped biphilic patterning in reducing the maximum size of departing droplets in DWC, we aim to quantify the controllability of droplet size distribution by varying the dimension of our patterns. In order to isolate the influence of the wettability pattern alone on the drop-size, we choose the Type II surface comprising of hydrophilic (mirror-finish Al) stripes interspaced by parallel superhydrophilic tracks. This way we eliminated the out-of-plane jumping of the droplets. The wettability contrast of the Type II surface was thus much less (≈0°-78°) compared to the Type I (≈0°-164°, although the geometric features were the same. We chose eight different widths of the philic region, viz., $\lambda$=400, 600, 800, 1000, 1250, 1500, 2000, and 2500 μm, offering the space for sustained heterogeneous nucleation and DWC). For the first four cases, the intervening superhydrophilic tracks were 300 μm wide, while it was 400 μm for the rest (this was done to accommodate the extra liquid drained from the larger catchment areas for larger $\lambda$ cases). A 12 mm×3 mm superhydrophilic patch was etched at the bottom of each biphilic design patterns to accumulate the drained condensate. All the substrates were tested in a condensing environment at 20° C. DBT and 80% RH over a duration of 1 hr. FIG. 23(*a*) shows the variation of droplet size for different values of $\lambda$. Droplet size in the philic surface of the unpatterned/monophilic regions (the region between the two patterned areas for each case in FIG. 23(*a1*)-(*a4*)) are found to be much larger than the same observed on the philic strips of the patterned regions. It is also clear from the figures that the maximum size of the departing droplets on the philic stripes (the less wettable ones compared to the superhydrophilic tracks) increased with the stripe width $\lambda$. To quantify, we took images every one minute for a duration of thirty minutes in a steady condensation scenario and analyzed them using an in-house MATLAB-based image analysis software. Maximum droplet size in each philic strip for each design was calculated through image processing. More than 300 data points were collected for each value of $\lambda$ and distribution of the data is represented in a box and whisker plot (FIG. 23(*b*)). The box plot presents the median, lower and upper quartiles (25th and 75th percentiles, respectively) of the data. The average maximum departing droplet diameter is plotted in FIG. 23(*c*). A linear relationship with $\lambda$ up to 2000 μm is observed for both the median and average $D_{max}$ values in FIGS. 23(*b*) and (*c*), respectively, indicating that the maximum droplet size is about 42% of the philic strip width. Beyond $\lambda$=2000 μm, the change in $D_{max}$ tapers off. The box C in FIG. 23(*b*) and the white line in gray band (standard deviation) in FIG. 23(*c*) denote the $D_{max}$ data for the unpatterned monophilic region, which is ~1125±319 μm. This provides clear evidence that the maximum droplet size can be controlled effectively with a parallel strip-like biphilic patterns. The average droplet size came out to be roughly 40%± of different values of $\lambda$.

Example 14

Water Collection Enhancement

In order to estimate how this technique of controlling the maximum droplet size eventually helps in improving DWC heat transfer, we conducted a series of condensation experiments. Tests were performed under two different environment conditions: 20° C. DBT, 80% RH ($T_{dew-point}$~16.45° C.) and 35° C. DBT-80% RH ($T_{dew-point}$~31.02° C.). Condensation on a mirror finish aluminum plate was used as a control case and exposed it in condensing environment for over 20 hours in 2~3 hour spells. Condensate drained due to gravity was collected and weighed. Next, we tested a Type II surface of same size having straight line patterns comprising philic (less wettable) stripes of $\lambda$=1200 μm interspaced by superhydrophilic tracks of 800 μm. The patterning pitch (distance between two consecutive philic strips) was so chosen that the ratio of philic to superhydrophilic areas was 3:2. For the bare plate, condensate collection rates were 0.69±0.01 and 1.61±0.01 L m$^{-2}$ h$^{-1}$ for the two operating conditions (i.e., 20° C. DBT, 80% RH and 35° C. DBT, 80% RH, respectively). The overall heat transfer in the process has both sensible and latent components. While the driving temperature difference for the formal part is the difference between the ambient DBT ($T_\infty$) and the substrate temperature ($T_s$), the latter is caused by the difference between the ambient wet bulb temperature (WBT, $T_{\infty W}$) and $T_s$. The latent contribution of the overall HTCs is evaluated as $$\text{HTC}=m_v h_{fg}/(T_{\infty W}-T_s) \qquad (5)$$

Figure 24:
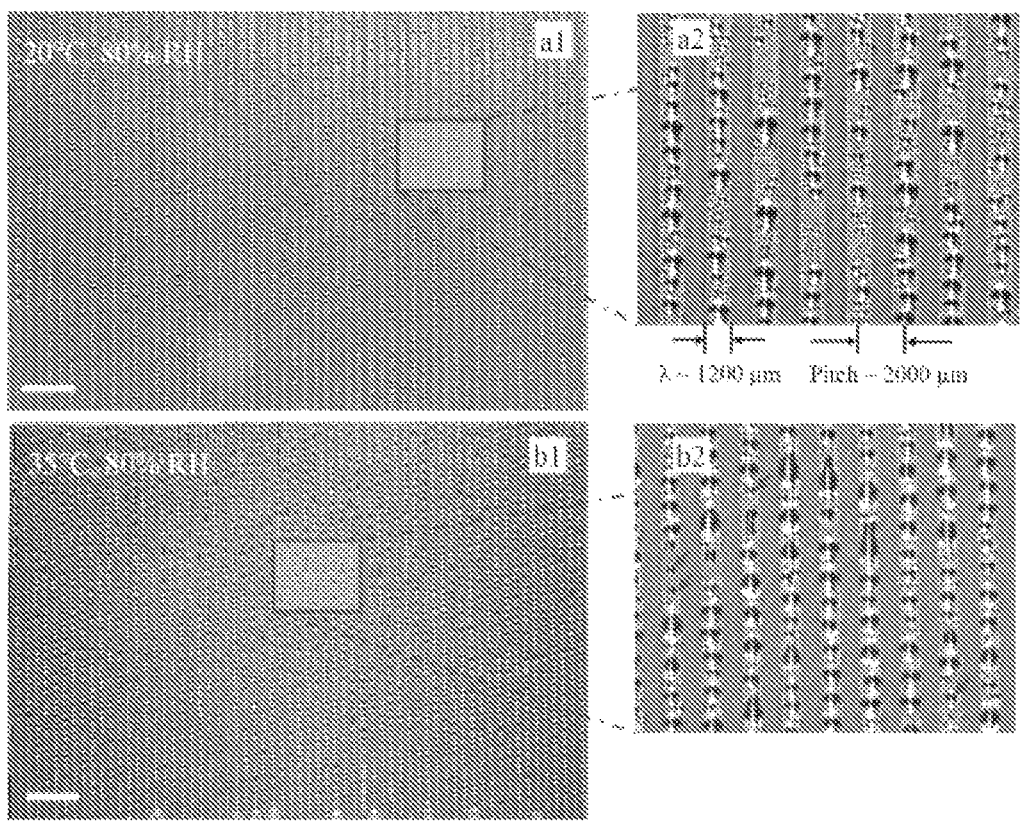
FIG. 24 shows Type II substrates with straight line wettability patterns fabricated and tested in a condensation chamber for two different conditions 20° C., 80% RH (a1), and 35° C., 80% RH (b1). (a2) and (b2) are zoomed in images of the above. The dimensions of the simple design are shown in (a2). The greater presence of water vapor in the atmosphere for (b1) is substantiated by visually observing higher number of droplets formed (b2) as compared to the number of droplets in (a2). Red arrows in (b2) show residual droplets after incomplete capillary pumping.

The average surface temperatures of the bare plates at $T_\infty$=20 and 35° C. cases were 2.2±0.4, and 18.2±0.5° C., respectively, while the measured average HTC were 30.6±1.0 and 78.8±1.9 W m$^{-2}$ K$^{-1}$, respectively. With the use of wettability patterned substrates, both the condensate collection and the latent heat transfer coefficient increased by 18% for the ambient condition of 20° C. DBT, 80% RH. However, the improvement was found to be less (~3.5%) for the case of the 35° C. DBT, 80% RH. In both the cases, the condensing plate temperature remained within a ±0.5° C. band, which was within the thermocouple error limits. The reduction in heat transfer improvement at elevated humidity ratio can be attributed to the greater difficulty in the drainage of the condensate from the philic (less wettable) strips to the superphilic tracks. FIG. 24 shows the comparison of droplet morphology on the patterned surface after 2 hours of condensation. Clearly, the largest droplet size on the philic strips for the 20° C. DBT, 80% RH (FIG. 24(*a*)) were smaller than those for the 35° C. DBT-80% RH case (FIG. 24(*b*)). Zoomed-in views in FIG. 24(*b2*) shows that the droplets even tend to deviate from circular footprint, growing longitudinally between the superphilic tracks. The superphilic strips meant for draining the condensate by hemiwicking and capillary pumping were in this case more "filled up," leading to a reduction in the droplet drainage rate from the philic strips. Apparently, with higher humidity ratio (the 35° C. DBT-80% RH case) several condensate droplets that grew to touch the superphilic tracks exhibited only partial drainage (leaving residual droplets behind on the less wettable strips, as shown by the red arrows in FIG. 24(*b2*)) and offered less rejuvenation than that in FIG. 24(a2)). Thus the drainage capacity of the superphilic tracks emerged as the rate limiting factor at high humidity ratio.

There are two important features to note in this context. The observed heat transfer improvement was realized in spite of two adverse factors firstly, the non-condensable gases (present in our experiments) offered a significant thermal resistance to mask off any improvement brought in by limiting the maximum droplet size, and second, the improvement was achieved even after devoting ~40% of the substrate for the superhydrophilic tracks (where the FWC has taken place, leaving only 60% area for DWC). The biphilic design in FIG. 24 offers ~10.7 m length of wettability transition line (across which the liquid droplets are swept away from the philic regions) on the ~108 cm$^2$ plate area. Designing these tracks wider could be an option to increase their condensate drainage capacity, but that at the same time would decrease the available philic area (where sustained heterogeneous nucleation and DWC takes place at mild conditions) and the length of transition line per unit area of the substrate. The latter two effects are detrimental enough (for the overall condensation rate) so we chose to discard the idea of widening the superhydrophilic tracks to buttress condensate drainage.

Example 15

Designs for Pumpless Removal of Condensate

Figure 25:
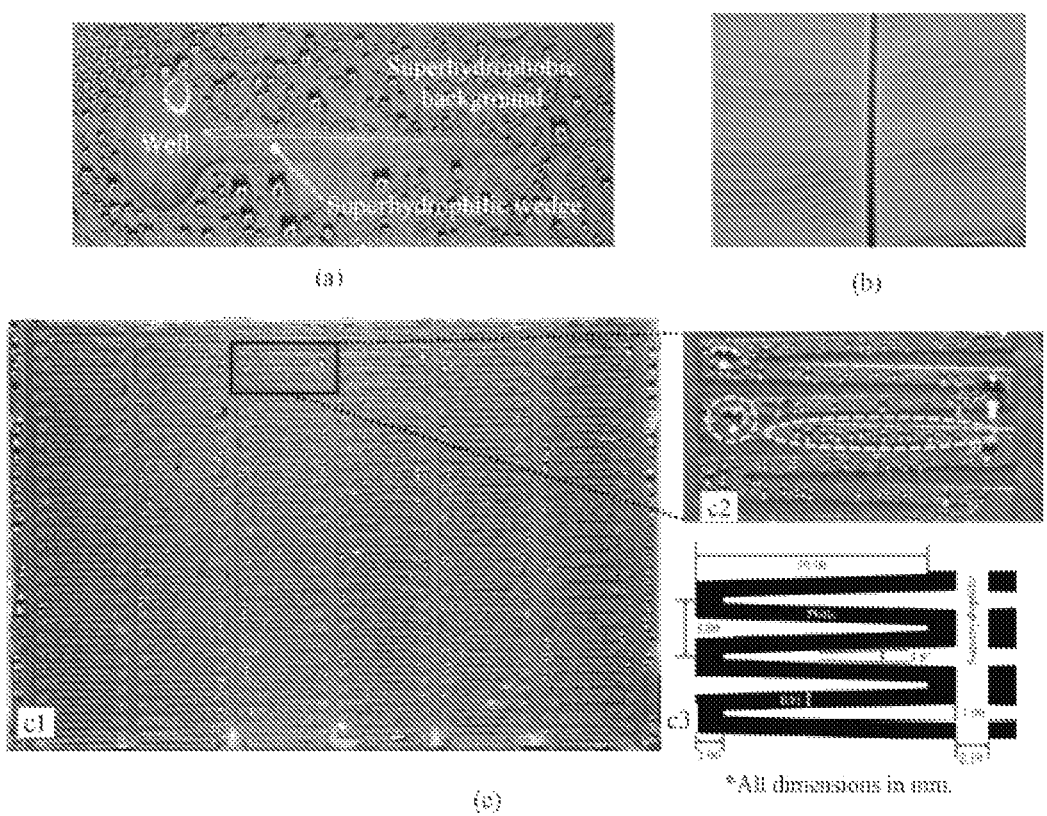
FIG. 25 shows (a) wedge shaped superhydrophilic track that aids pumpless transport of condensate from its narrow end to the wider end. The bulged puddle at the elliptic superhydrophilic well at the broad end of the wedge holds the condensate drained through the track. (b) A typical monocotyledon leaf vein structure of banana leaf (*Musa paradascica*). (c1) Condensation on interdigitated wettability-patterned design inspired from banana leaf vein network layout (image taken after three hours of condensation for the same condition as in FIG. 7(*a*)). Insets: (c2) Condensate droplet distribution on the philic bands; a superhydrophilic tapered wedge track is shown in red highlight; note the difference in droplet size in the two yellow-highlighted philic regions which have different local widths. (c3) The key dimensions of the interdigitated design.

The foregoing discussion provides evidence that controlling the maximum droplet size using biphilic patterns on the condenser surface indeed can lead to an enhancement in condensation heat transfer rate; on the other hand, it also highlights the need to ensure adequate drainage of condensate using the minimum possible area for the superphilic tracks. Our prior work has demonstrated that designing the superhydrophilic tracks with a small tapering angle gives them the ability to achieve rapid pumpless transport of liquid on wettability-patterned surfaces. The same design is hypothesized to work for transporting condensate from a condensing surface. FIG. 25(a) shows a wedge shaped superhydrophilic track on the condensing surface transporting the collected condensate from the narrow end to the wider one. The liquid pool created at the downstream (the collection well was produced by patterning an elliptic superhydrophilic region) shows evidence of condensate pumping. For a large condensing surface, the ideal design should offer a suitable network of these wedges for sustained condensate drainage. In an effort to improve the performance of our condensing surfaces, we take inspiration from Nature: the vein arrangement of leaves in plants presents a typical 2-dimensional network that offers an optimal liquid (sap) transport system. Considering the closest analogy to the parallel-striped wettability patterns presented in the foregoing sections, we adopt a monocotyledon leaf venation pattern, usually found in banana leaves (See FIG. 25(b)). For comparing its condensation performance with the parallel-striped wettability patterned plate (FIG. 24), the ratio of philic area to superhydrophilic area was kept the same, i.e., 3:2. However, the bio-inspired design had a larger net available length of wettability transition, ~11.9 m (as compared to 10.7 m for the parallel stripe design) for the same plate area. This offered a greater possibility of droplets being drained to the superhydrophilic tracks. To compare the efficacy of the bio-inspired wettability pattern on the overall DWC, we exposed the surface to condensing environment similar to the one used for straight line patterns. Droplet distribution on the philic strips of the bioinspired interdigitated pattern is shown in the inset FIG. 25(c2). Except the tip region of each wedge track, where the local width of the philic region was larger, condensate droplets appeared consistently smaller than the control case (the bare aluminum plate). FIG. 25(c3) shows the key dimensions of the design.

Figure 26:
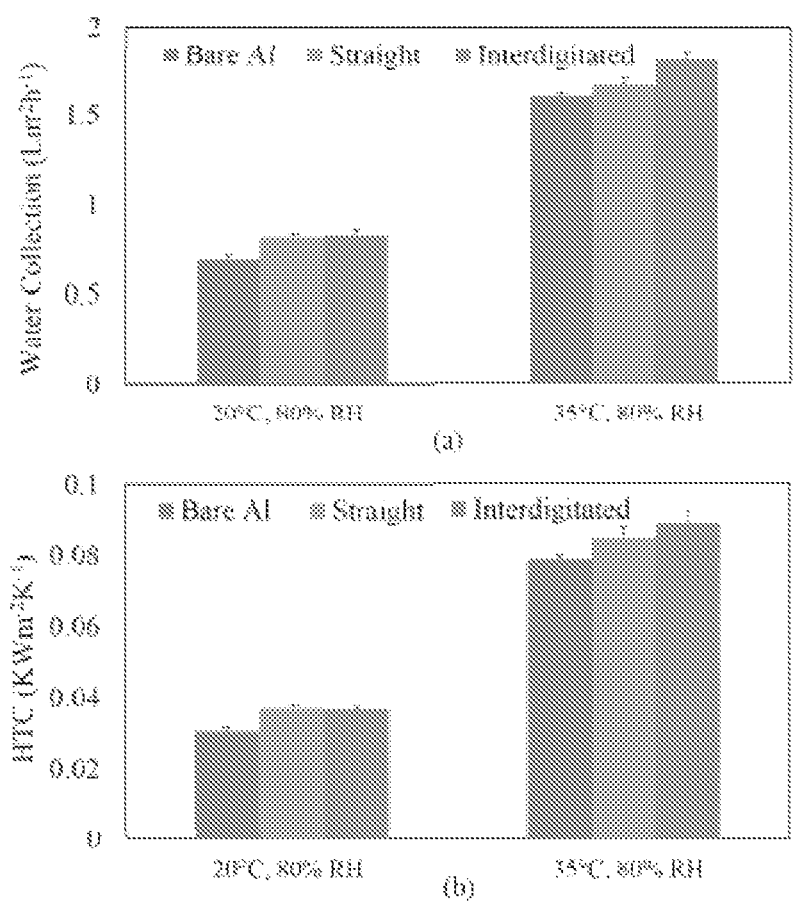
FIG. 26 shows bar graphs of the percentage improvement in condensation in terms of condensate collection rate (a) and the latent heat transfer coefficient (HTC, b) for Type II surface in two different environments for the monolithic control case (bare Al), biphilic with straight line and bioinspired interdigitated wettability patterns. Both the patterned surfaces performed better than the control surface for 20° C. DBT-80% RH and 35° C. DBT-80% RH conditions. The interdigitated pattern is more effective in higher vapor loading situations (35° C. DBT-80% RH) compared to the straight line patterns. The improvement can be attributed, at least in part, to the geometric shape of the wettability patterning of the substrate, which drains the condensate more effectively.

FIG. 26 compares the condensation and heat transfer performance of the bioinspired interdigitated pattern design with those of the control case (the monophilic bare Al plate) and the straight philic-superphilic patterned substrates. Each data point on FIG. 26 is obtained from at least 5 multiple hour (2-5 hrs) runs; the error bars denote standard deviation. For the interdigitated pattern an overall 19% improvement in condensate collection and ~20% improvement in HTC compared to the control case for 20° C. DBT-80% RH was observed. This performance was comparable to the straight line pattern case. However, at 35C DBT-80% RH condition, the bioinspired interdigitated pattern showed ~12.5% improvement in water collection and HTC over the base case. This translated to an extra ~9% improvement in water collection and 5% improvement in HTC by using bioinspired interdigitated patterns compared to straight line patterns. Therefore, the bioinspired design would be preferred under more adverse condensing conditions (the higher heat-flux scenarios), when other types of wettability patterns (or monophilic designs) would give lower DWC performance due to poor condensate drainage and large droplet size.

We claim:

1. A device comprising:
a substrate configured for gravity-independent pumpless transport of fluids,
wherein the substrate includes a coating surface dispersed thereon, the coating surface comprising a hydrophilic track on a hydrophobic surface; and
wherein the hydrophilic track is a trapezoidal-shaped track having a narrower end and a wider end, the trapezoidal-shaped track being capable of transporting fluid from the narrower end to the wider end of the trapezoidal-shaped track at a speed of from 1 mm/s to 500 mm/s.

2. The device of claim 1, wherein the coating surface is biphilic and has a surface of two alternating domains.

3. The device of claim 2, wherein the two domains are superhydrophilic and hydrophobic or superhydrophilic and superhydrophobic.

4. The device of claim 1, wherein the substrate is selected from the group consisting of metal, glass, fabric, paper, quartz, and silicon.

5. The device of claim 1, wherein the wider end of the trapezoidal-shaped track has a width of between 500 µm and 2 cm.

6. The device of claim 1, wherein the coating surface is a condensing surface capable of allowing gaseous components to condense as a liquid onto the condensing surface when a temperature of the condensing surface is below a wet bulb temperature of an environment.

7. The device of claim 1, wherein the hydrophilic track is confined by the hydrophobic surface.

8. The device of claim 1, wherein the coating surface is biphilic and the hydrophilic track is a superhydrophilic track.

9. The device of claim 8, wherein the narrower end of the trapezoidal-shaped track has a width of from 10 µm to 500 µm.

10. The device of claim 1, wherein the hydrophobic surface includes a nanoparticle filler and a fluoroacrylic copolymer dispersion.

\* \* \* \* \*